US011344539B2

(12) United States Patent
Nishino et al.

(10) Patent No.: US 11,344,539 B2
(45) Date of Patent: May 31, 2022

(54) THERAPEUTIC OR PROPHYLACTIC DRUG FOR DEMENTIA

(71) Applicants: NATIONAL UNIVERSITY CORPORATION TOTTORI UNIVERSITY, Tottori (JP); Takeshi Nishino, Tokyo (JP); Ken Okamoto, Yokohama (JP); Teijin Pharma Limited, Tokyo (JP)

(72) Inventors: Takeshi Nishino, Tokyo (JP); Shinsuke Kato, Yonago (JP); Masako Kato, Yonago (JP); Hidenori Suzuki, Tokyo (JP); Ken Okamoto, Tokyo (JP)

(73) Assignees: NATIONAL UNIVERSITY CORPORATION TOTTORI UNIVERSITY, Tottori (JP); Takeshi Nishino, Tokyo (JP); Ken Okamoto, Yokohama (JP); Tejin Pharma Limited, Tokyo (JP)

( * ) Notice: Subject to any disclaimer, the term of this patent is extended or adjusted under 35 U.S.C. 154(b) by 796 days.

(21) Appl. No.: 15/998,949

(22) PCT Filed: Feb. 17, 2017

(86) PCT No.: PCT/JP2017/006007
§ 371 (c)(1),
(2) Date: Aug. 17, 2018

(87) PCT Pub. No.: WO2017/142091
PCT Pub. Date: Aug. 24, 2017

(65) Prior Publication Data
US 2021/0205285 A1 Jul. 8, 2021

(30) Foreign Application Priority Data

Feb. 19, 2016 (JP) ............................ JP2016-030048

(51) Int. Cl.
*A61K 31/4439* (2006.01)
*A61P 25/28* (2006.01)
*A61K 9/00* (2006.01)
*A61K 31/426* (2006.01)
*A61K 31/427* (2006.01)

(52) U.S. Cl.
CPC ........ *A61K 31/4439* (2013.01); *A61K 9/0053* (2013.01); *A61K 31/426* (2013.01); *A61K 31/427* (2013.01); *A61P 25/28* (2018.01)

(58) Field of Classification Search
CPC ............................ A61K 31/4439; A61P 25/28
See application file for complete search history.

(56) References Cited

U.S. PATENT DOCUMENTS 5,614,520 A 3/1997 Kondo et al.
8,318,792 B2 * 11/2012 Nishino .............. A61K 31/426
514/406

2005/0239807 A1 10/2005 Stamler et al.
2014/0249318 A1 9/2014 Nakatsuji et al.
2015/0005506 A1 1/2015 Hisatome et al.
2015/0376174 A1 12/2015 Kawana et al.
2016/0039784 A1 2/2016 Kawana et al.
2017/0217948 A1 8/2017 Shirakura et al.

FOREIGN PATENT DOCUMENTS

| CA | 2 955 577 A1 | 2/2016 |
|---|---|---|
| CN | 1596110 A | 3/2005 |
| CN | 101575335 A | 11/2009 |
| EP | 0 513 379 A1 | 11/1992 |
| JP | 2003-201255 A | 7/2003 |
| JP | 2004-536037 A | 12/2004 |
| JP | 2005-508974 A | 4/2005 |
| JP | 2006-522164 A | 9/2006 |
| JP | 2009-503094 A | 1/2009 |
| JP | 2010-509372 A | 3/2010 |
| WO | 92/09279 A1 | 6/1992 |
| WO | 02/068417 A1 | 9/2002 |
| WO | 03/031435 A1 | 4/2003 |
| WO | 03/037324 A1 | 5/2003 |
| WO | 2004/089303 A2 | 10/2004 |
| WO | 2007/019153 A2 | 2/2007 |
| WO | 2007/086931 A1 | 8/2007 |
| WO | 2008/064015 A1 | 5/2008 |
| WO | 2010/071865 A1 | 6/2010 |
| WO | 2013/050996 A2 | 4/2013 |
| WO | 2013/054940 A1 | 4/2013 |
| WO | 2013/111870 A1 | 8/2013 |
| WO | 2014/119681 A1 | 8/2014 |
| WO | 2014/157740 A1 | 10/2014 |
| WO | 2016/017699 A1 | 2/2016 |

(Continued)

OTHER PUBLICATIONS

Zhang, et al., "Allopurinol protects against ischemic insults in a mouse model of cortical microinfarction.", Brain Research, 2015, vol. 1622, pp. 361-367 (7 pages total).
International Search Report, dated May 16, 2017, issued by the International Searching Authority in counterpart International application No. PCT/JP2017/006007.
Toshifumi Kishimoto, Shigeki Takahashi, Psychiatry, STEP Series psychiatry, Second Edition, pp. 103-104, Kaiba shobo, 2008 (4 pages total).
Takashi Asada, "Present status of epidemiology for dementia in Japan", Journal of Clinical and Experimental Medicine, supplementary volume "dementia," Ishiyaku Publishers, pp. 5-10, 2011 (8 pages total).

(Continued)

*Primary Examiner* — Kamal A Saeed

(74) *Attorney, Agent, or Firm* — Sughrue Mion, PLLC

(57) ABSTRACT

The present invention provides a therapeutic agent or a prophylactic agent of dementia containing xanthine oxidase inhibitor such as a compound represented in formula (I), (II), (III) or (IV), or a pharmaceutically acceptable salt thereof as an active ingredient.

3 Claims, 10 Drawing Sheets

(56) References Cited

FOREIGN PATENT DOCUMENTS

WO    2016/017826  A1    2/2016
WO    2017/081609  A1    5/2017

OTHER PUBLICATIONS

Schumacher, et al., "Effects of febuxostat versus allopurinol and placebo in reducing serum urate in subjects with hyperuricemia and gout: a 28-week, phase III, randomized, double-blind, parallel-group trial," Arthritis and Rheumatism, 2008, vol. 59, No. 11. pp. 1540-1548 (11 pages total).

Fatokun, et al., "Hydrogen peroxide mediates damage by xanthine and xanthine oxidase in cerebellar granule neuronal cultures", Neurosci. Lett., 2007, vol. 416, No. 1, pp. 34-38 (7 pages total).

Lara, et al.,"Allopurinol for the treatment of aggressive behaviour in patients with dementia", Case report 53, International Clinical Psychopharmacology, 2003, vol. 18, No. 1, pp. 53-55 (5 pages total).

\* cited by examiner

Human Alzheimer's disease

Mouse model with Alzheimer's disease

Senile Plaque

Neurofibillary tangle

THERAPEUTIC OR PROPHYLACTIC DRUG FOR DEMENTIA

CROSS REFERENCE TO RELATED APPLICATIONS

This application is a National Stage of International Application No. PCT/JP2017/006007, filed Feb. 17, 2017, claiming priority based on Japanese Patent Application No. 2016-030048, filed Feb. 19, 2016.

FIELD

The present invention relates to a therapeutic agent or a prophylactic agent for dementia. Specifically, the present invention relates to a therapeutic agent or a prophylactic agent for dementia containing a xanthine oxidase inhibitor as an active ingredient, such as a 2-phenylthiazole compound or a pharmaceutically acceptable salt thereof having an excellent effect of improving cognitive function.

BACKGROUND

Dementia can be defined as the condition when mental ability, once developed, declines by some kinds of acquired causes, presenting difficulties of social adjustment. Dementia-related diseases are classified as neurodegenerative diseases, vascular dementia, prion diseases, infectious diseases, metabolism/endocrine diseases, trauma, diseases in the field of brain surgery and poisoning diseases (NPL 1). As of 2010, there are about 2,100,000 patients with dementia in Japan, and the prevalence of dementia in elderly people over the age of 65 is thought to be approximately 8 to 10% or more. This fact is recognized as a huge problem in today's worldwide aging society (NPL 2). Among the underlying diseases of dementia, Alzheimer's disease accounts for approximately 35% (also referred to as "Alzheimer's disease" or "AD"). Approximately 15% of dementia cases are a mixed type of AD and a cerebrovascular type. The treatment of AD patients has become a significant challenge at the social end (NPL 2). Currently, a cholinesterase inhibitor such as donepezil, galanthamine, rivastigmine, and an NMDA receptor blocker such as memantine are used as therapeutic agents for AD, but their effects are not sufficient to cure AD.

As disclosed in PTL 1, it is known that a xanthine oxidase inhibitor exhibits its efficacy in preventing and treating AD with the concomitant administration of an NADPH oxidase inhibitor and/or caspase inhibitor. However, it is not known whether a xanthine oxidase inhibitor alone can be a therapeutic or a prophylactic agent for AD.

It is known that 2-phenyl thiazole compounds such as 2-(3-cyano-4-isobutyl oxyphenyl)-4-methyl-5-thiazole carboxylic acid (generic name: Febuxostat) used in the present invention have the effect of reducing uric acid levels by exerting a strong inhibitory effect of xanthine oxidase, thus those compounds are used as therapeutic agents for hyperuricemia and gout (NPL 3). Also, in addition to hyperuricemia and gout, it is found that they can be therapeutic agents for treating diseases such as renal diseases (PTL 2), hypertension (PTL 3), multiple sclerosis (PTL 4), and diabetic mellitus (PTL 5). Also, it is known that an azolebenzene compound, a pyrazole compound, and an azole carboxylic acid compound used in the present invention have the effect of reducing uric acid levels by exhibiting a strong inhibitory effect of xanthine oxidase, thus they are used as therapeutic agents for hyperuricemia and gout (PTL's 6, 7 and 8). However, it is not known if these compounds can be used as a therapeutic agent for dementia such as AD.

CITATION LIST

Patent Literature

PTL 1: Japanese Unexamined Patent Application Publication No. 2003-201255
PTL 2: Japanese Translation of PCT International Application Publication No. 2010-509372
PTL 3: Japanese Translation of PCT International Application Publication No. 2009-503094
PTL 4: WO2013/054940
PTL 5: WO2013/111870
PTL 6: WO2014/119681
PTL 7: WO2014/157740
PTL 8: WO2016/017699

Non Patent Literature

NPL 1: Toshifumi Kishimoto, Shigeki Takahashi edition, STEP Series psychiatry Second Edition, p 103-104, Kaiba shobo, 2008
NPL 2: Takashi Asada, Journal of Clinical and Experimental Medicine supplementary volume, "dementia" Ishiyaku Publishers, p 5-10, 2011.
NPL 3: Arthritis and Rheumatism. 2008, 59:1540-1548

SUMMARY

Technical Problem

An object of the present invention is to provide a new therapeutic or prophylactic agent for dementia.

Solution to Problem

The present inventors have extensively studied on such a subject and found that a 2-phenylthiazole compound represented by Formula (I), an azolebenzene compound represented by Formula (II), a pyrazole compound represented by Formula (III) or an azolecarboxylic compound represented by Formula (IV), or a pharmaceutically acceptable salt thereof has an effect of treating or preventing dementia such as AD.

That is, the present invention is as follows.
(1) A therapeutic agent or a prophylactic agent for dementia comprising: a 2-phenylthiazole compound represented by Formula (I), an azolebenzene compound represented by Formula (II), a pyrazole compound represented by Formula (III) or an azolecarboxylic compound represented by Formula (IV), or a pharmaceutically acceptable salt thereof as an active ingredient:

A 2-phenylthiazole compound represented by Formula (I):

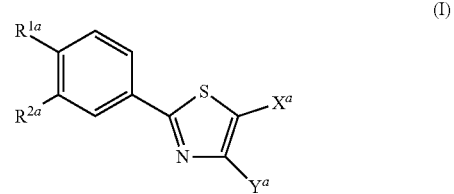

(wherein

R$^{1a}$ represents a C1-C8 alkoxy group, a morpholino group, a 4-methylpiperazin-1-yl group or a piperidino group, R$^{2a}$ represents a nitro group or a cyano group, X$^a$ represents a carboxyl group or a C2-C7 alkoxycarbonyl group, Y$^a$ represents a hydrogen atom or a C1-C6 alkyl group.)

An azolebenzene compound represented by Formula (II):

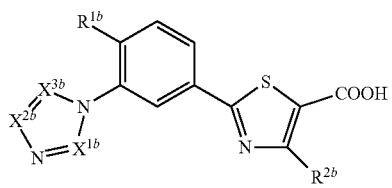

(II)

(wherein

R$^{1b}$ represents OR$^b$, NR$^b$R$^{b\iota}$ which may form a ring, or SR$^b$, wherein R$^b$ and R$^{b\iota}$ independently represent a hydrogen atom, a C1-C8 alkyl group optionally substituted with one or a plurality of C1-C8 alkoxy groups, halogen atoms or hydroxyl groups, an aryl group optionally substituted with one or a plurality of C1-C8 alkyl groups, C1-C8 alkoxy groups or halogen atoms, or a heteroaryl group optionally substituted with one or a plurality of C1-C8 alkyl groups, C1-C8 alkoxy groups, or halogen atoms, R$^{2b}$ represents a hydrogen atom or a C1-C8 alkyl group, X$^{1b}$, X$^{2b}$ and X$^{3b}$ independently represent CR$^{3b}$ or a nitrogen atom, or X$^{1b}$ represents CR$^{3b}$ or a nitrogen atom and X$^{2b}$ and X$^{3b}$ are taken together to form a benzene ring, R$^{3b}$ represents a hydrogen atom or a C1-C8 alkyl group.).

A pyrazole compound represented by Formula (III):

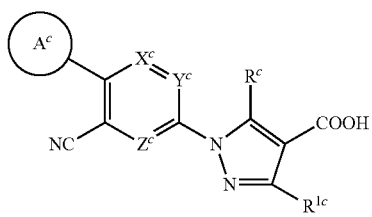

(III)

(wherein

A$^c$ represents a C6-C10 aryl group of or a heteroaryl group, wherein the aryl or the heteroaryl group is unsubstituted or optionally substituted with 1 to 3 groups of Q$^c$, wherein the Q$^c$ is the same or different from each other, and is selected from the group consisting of halogen atom, —CN, —NO$_2$, C1-C6 alkyl group, C3-C7 cycloalkyl group, C1-C6 halogenoalkyl group, phenyl group, —CH$_2$—O—R$^{2c}$, —O—R$^{2c}$, —O—(C1-C6 halogenoalkyl), —O-benzyl, —O-phenyl, —O—CO—R$^{2c}$, —NR$^{3c}$R$^{4c}$, —NH—CO—R$^{2c}$, —CO$_2$—R$^{2c}$, —CO—R$^{2c}$, —CO—NR$^{3c}$R$^{4c}$, —NH—SO$_2$—R$^{2c}$, —CO-aryl, —S—R$^{2c}$, —SO$_2$—(C1-C6 alkyl) and —SO$_2$-phenyl, X$^c$, Y$^c$ and Z$^c$ represent a CR$^{5c}$ or a nitrogen atom, wherein one of X$^c$, Y$^c$ and Z$^c$ is a nitrogen atom and other two are CR$^{5c}$, R$^c$ represents a hydrogen atom or a C1-C6 alkyl group, R$^{1c}$ represents a hydrogen atom, an amino group or a C1-C6 alkyl group, R$^{2c}$ represents a hydrogen atom or a C1-C6 alkyl group, R$^{3c}$ and R$^{4c}$ are the same or different from each other, and represent a hydrogen atom or a C1-C6 alkyl group, wherein R$^{3c}$ and R$^{4c}$ may be taken together to form a monocyclic nitrogen-containing saturated heterocycle to which the nitrogen atom is bound with R$^{3c}$ and R$^{4c}$, R$^{5c}$ represents a hydrogen atom, a halogen atom or a C1-C6 alkyl group.)

An azolecarboxylic compound represented by Formula (IV):

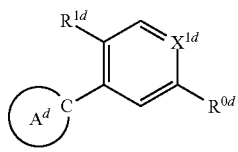

(IV)

(wherein

R$^{0d}$ represents the following R$^{01d}$ or R$^{02d}$:

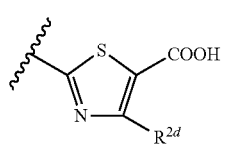

(R$^{01d}$)

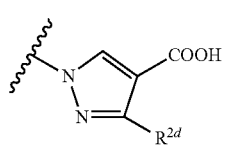

(R$^{02d}$)

R$^{1d}$ represents an aryl group optionally substituted with one or a plurality of C1-C6 alkyl groups, C1-C6 alkoxy groups or halogen atoms, OR$^d$, NR$^d$R$^{d\iota}$ optionally forming a ring, or SR$^d$, wherein R$^d$ and R$^{d\iota}$ independently represent a hydrogen atom, a C1-C8 alkyl group optionally substituted with one or a plurality of C1-C8 alkoxy groups, halogen atoms or hydroxyl groups, an aryl group optionally substituted with one or a plurality of C1-C6 alkyl groups, C1-C6 alkoxy groups, halogen atoms, or cyano groups, or a heteroaryl group optionally substituted with one or a plurality of C1-C6 alkyl groups, C1-C6 alkoxy groups, or halogen atoms.

R$^{2d}$ represents a hydrogen atom, an amino group or a C1-C8 alkyl group optionally substituted with one or a plurality of halogen atoms, X$^{1d}$ represents CR$^{3d}$ or a nitrogen atom, wherein R$^{3d}$ represents a hydrogen atom or a halogen atom, Ring A$^d$ represents a 5- or 6-membered monocycle heteroarene optionally substituted with 1 to 4 groups selected from the group consisting of a C1-C6 alkyl group optionally substituted with one or a plurality of C1-C3 alkoxy groups or halogen atoms, a C1-C6 alkoxy group optionally substituted with one or a plurality of halogen atoms, and a halogen atom.).

(2) The therapeutic agent or the prophylactic agent according to (1), wherein the compound is 2-(3-cyano-4-isobutyloxyphenyl)-4-methyl-5-thiazolecarboxylic acid or a pharmaceutically acceptable salt thereof.

(3) The therapeutic agent or the prophylactic agent according to (1), wherein the compound is selected from Compounds B-1 to B-42 described in the specification, or a pharmaceutically acceptable salt thereof.

(4) The therapeutic agent or the prophylactic agent according to (1), wherein the compound is selected from Compounds C-1 to C-7 described in the specification, or a pharmaceutically acceptable salt thereof.

(5) The therapeutic agent or the prophylactic agent according to (1), wherein the compound is selected from Compounds D-1 to D-3 described in the specification, or a pharmaceutically acceptable salt thereof.

(6) The therapeutic agent or the prophylactic agent according to any of (1) to (5), wherein the dementia is Alzheimer's dementia.

Advantageous Effects of Invention

The present invention provides a 2-phenylthiazole compound represented by Formula (I), an azolebenzene compound represented by Formula (II), a pyrazole compound represented by Formula (III) or an azolecarboxylic compound represented by Formula (IV), or a pharmaceutically acceptable salt thereof, enabling to treat or prevent dementia such as AD.

DESCRIPTION OF EMBODIMENTS

Figure 1:
FIG. 1 shows a photo of orally administrating to a mouse.

"Halogen atom" in the present invention means fluorine atom, chlorine atom, bromine atom and iodine atom.

"Alkyl group" in the present invention means a univalent saturated linear chain, cyclic or branched aliphatic hydrocarbon group.

"Alkylene group" in the present invention means a divalent group which is derived by removing a hydrogen atom at any position from the above "alkyl group".

"Alkoxy group" in the present invention means a univalent saturated linear chain, cyclic or branched aliphatic hydrocarbon oxy group.

"Alkoxycarbonyl group" in the present invention means a group consisting of the above-mentioned alkoxy group and a carbonyl group. "C2-C7 alkoxycarbonyl group" means a group consisting of a C1 to C6 alkoxy group and a carbonyl group.

"Aryl group" in the present invention means a monocyclic or bicyclic univalent aromatic hydrocarbon group having 6 to 10 carbon atoms.

"Heteroarene group" in the present invention means a monocyclic or bicyclic aromatic heterocycle having 1 to 5 hetero atoms selected from oxygen atom, sulfur atom and nitrogen atom. A "5- or 6-membered monocyclic heteroarene" means a 5- or 6-membered monocyclic one of the above-mentioned "heteroarene group".

"Heteroaryl group" in the present invention means a monocyclic or monovalent bicyclic aromatic heterocycle group having 1 to 5 hetero atoms selected from oxygen atom, sulfur atom and nitrogen atom.

"Alkyl group having 1 to 8 carbon atoms optionally substituted" in the present invention means alkyl group having 1 to 8 carbon atoms that may have one or a plurality of substituents at substitutable positions. When a plurality of substituents is present, each substituent may be the same or different. Other substituent "optionally substituted" has similar meaning.

In the present invention, when an alkyl group is substituted with an alkoxy group, the alkyl group and the alkoxy may be taken together to form an oxygen-containing saturated ring. Such rings include oxirane, oxetane, tetrahydrofuran, tetrahydropyran, and the like.

Examples of a 2-phenylthiazole compound represented by the following Formula (I):

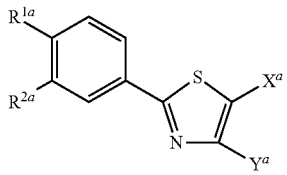

(wherein
R$^{1a}$ represents a C1-C8 alkoxy group, a morpholino group, a 4-methylpiperazin-1-yl group or a piperidino group,
R$^{2a}$ represents a nitro group or a cyano group,
X$^a$ represents a carboxyl group or a C2-C7 alkoxycarbonyl group,
Y$^a$ represents a hydrogen atom or a C1-C6 alkyl group.)
or a pharmaceutically acceptable salt thereof in the present invention include 2-(3-cyano-4-isobutyloxyphenyl)-4-methyl-5-thiazolecarboxylic acid (compound A).

The compound represented by Formula (II) can be prepared by the well-known method including the method described in WO92/09279.

In the above-mentioned Formula (I), preferable examples of "C1-C8 alkoxy group" in R$^{1a}$ include methoxy, ethoxy, n-propyloxy, n-butyloxy, isopropyloxy, isobutyloxy, sec-butyloxy, tert-butyloxy, isopentyloxy, neopentyloxy and the like. More preferably, isobutyloxy group is cited. R$^{1a}$ is preferably a C1-C8 alkoxy group, and more preferably an isobutyloxy group.

R$^{2a}$ is preferably cyano group.

Preferable examples of "C2-C7 alkoxycarbonyl group" in X$^a$ include methoxycarbonyl group, ethoxycarbonyl group and the like. X$^a$ is preferably a carboxyl group.

In the above-mentioned Formula (I), preferable examples of "C1-C6 alkyl group" in Y$^a$ include methyl, ethyl, propyl, isopropyl and the like. More preferably, methyl group is cited. Y$^a$ is preferably a C1-C6 alkyl group, and more preferably a methyl group.

Combination of substituent in the above-mentioned Formula (I) is preferably a combination of groups selected from preferable groups, and more preferably from more preferable groups.

A compound represented by Formula (I) is preferably the above-mentioned compound A.

The azolebenzene compound represented by the following Formula (II) in the present invention or pharmaceutically acceptable salts thereof is as follows:

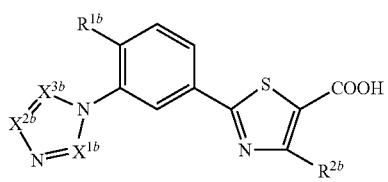

(wherein
R$^{1b}$ represents OR$^b$, NR$^b$R$^{b\prime}$ which may form a ring, or SR$^b$, wherein R$^b$ and R$^{b\prime}$ independently represent a hydrogen atom, a C1-C8 alkyl group optionally substituted with one or a plurality of C1-C8 alkoxy groups, halogen atoms or hydroxyl groups, an aryl group optionally substituted with one or a plurality of C1-C8 alkyl groups, C1-C8 alkoxy groups or halogen atoms, or a heteroaryl group optionally substituted with one or a plurality of C1-C8 alkyl groups, C1-C8 alkoxy groups, or halogen atoms.

R$^{2b}$ represents a hydrogen atom or a C1-C8 alkyl group.
X$^{1b}$, X$^{2b}$ and X$^{3b}$ independently represent CR$^{3b}$ or a nitrogen atom, or X$^{1b}$ represents CR$^{3b}$ or a nitrogen atom and X$^{2b}$ and X$^{3b}$ are taken together to form a benzene ring.)
The structure for the Formula (II), where X$^{2b}$ and X$^{3b}$ are taken together to form a benzene ring, is as follows:

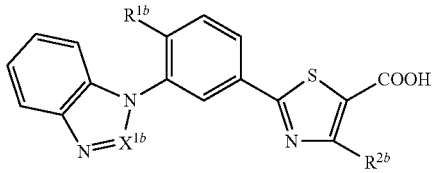

(R$^{3b}$ represents a hydrogen atom or a C1-C8 alkyl group.)
Examples of the azolebenzene compound represented by the Formula (II) or a pharmaceutically acceptable salt thereof include the following compounds:
(B-1) 2-[3-(1H-imidazol-1-yl)-4-(2-methylpropoxy)phenyl]-4-methyl-1,3-thiazole-5-carboxylic acid
(B-2) 4-methyl-2-[3-(2-methyl-1H-imidazol-1-yl)-4-(2-methylpropoxy)phenyl]-1,3-thiazole-5-carboxylic acid
(B-3) 2-[3-(1H-1,3-benzodiazol-1-yl)-4-(2-methylpropoxy)phenyl]-4-methyl-1,3-thiazole-5-carboxylic acid
(B-4) 4-methyl-2-[3-(3-methyl-1H-1,2,4-triazol-1-yl)-4-(2-methylpropoxy)phenyl]-1,3-thiazole-5-carboxylic acid
(B-5) 4-methyl-2-[4-(2-methylpropoxy)-3-(1H-1,2,4-triazol-1-yl)phenyl]-1,3-thiazole-5-carboxylic acid
(B-6) 4-methyl-2-[3-(5-methyl-1H-1,2,4-triazol-1-yl)-4-(2-methylpropoxy)phenyl]-1,3-thiazole-5-carboxylic acid
(B-7) 4-methyl-2-[4-(propan-2-yloxy)-3-(1H-1,2,3-triazol-1-yl)phenyl]-1,3-thiazole-5-carboxylic acid
(B-8) 4-methyl-2-[4-(2-methylpropoxy)-3-(1H-1,2,3-triazol-1-yl)phenyl]-1,3-thiazole-5-carboxylic acid
(B-9) 2-[4-(2,2-dimethylpropoxy)-3-(1H-1,2,3-triazol-1-yl)phenyl]-4-methyl-1,3-thiazole-5-carboxylic acid
(B-10) 2-[4-(cyclobutylmethoxy)-3-(1H-1,2,3-triazol-1-yl)phenyl]-4-methyl-1,3-thiazole-5-carboxylic acid
(B-11) 2-[4-(propan-2-yloxy)-3-(1H-1,2,3-triazol-1-yl)phenyl]-1,3-thiazole-5-carboxylic acid
(B-12) 2-[4-(2-methylpropoxy)-3-(1H-1,2,3-triazol-1-yl)phenyl]-1,3-thiazole-5-carboxylic acid
(B-13) 4-methyl-2-[4-(propan-2-yloxy)-3-(1H-1,2,3,4-tetrazol-1-yl)phenyl]-1,3-thiazole-5-carboxylic acid
(B-14) 4-methyl-2-[4-(2-methylpropoxy)-3-(1H-1,2,3,4-tetrazol-1-yl)phenyl]-1,3-thiazole-5-carboxylic acid
(B-15) 2-[4-(2,2-dimethylpropoxy)-3-(1H-1,2,3,4-tetrazol-1-yl)phenyl]-4-methyl-1,3-thiazole-5-carboxylic acid
(B-16) 2-[4-(cyclobutylmethoxy)-3-(1H-1,2,3,4-tetrazol-1-yl)phenyl]-4-methyl-1,3-thiazole-5-carboxylic acid
(B-17) 2-[4-(cyclopentyloxy)-3-(1H-1,2,3,4-tetrazol-1-yl)phenyl]-4-methyl-1,3-thiazole-5-carboxylic acid
(B-18) 2-[4-(3-hydroxy-2-methylpropoxy)-3-(1H-1,2,3,4-tetrazol-1-yl)phenyl]-4-methyl-1,3-thiazole-5-carboxylic acid
(B-19) 2-[4-(2-hydroxy-2-methylpropoxy)-3-(1H-1,2,3,4-tetrazol-1-yl)phenyl]-4-methyl-1,3-thiazole-5-carboxylic acid
(B-20) 2-[4-(propan-2-yloxy)-3-(1H-1,2,3,4-tetrazol-1-yl)phenyl]-1,3-thiazole-5-carboxylic acid (B-21) 2-[4-(2-methylpropoxy)-3-(1H-1,2,3,4-tetrazol-1-yl)phenyl]-1,3-thiazole-5-carboxylic acid
(B-22) 4-methyl-2-[4-phenoxy-3-(1H-1,2,3,4-tetrazol-1-yl)phenyl]-1,3-thiazole-5-carboxylic acid
(B-23) 2-[4-(2-fluorophenoxy)-3-(1H-1,2,3,4-tetrazol-1-yl)phenyl]-4-methyl-1,3-thiazole-5-carboxylic acid
(B-24) 2-[4-(2-methoxyphenoxy)-3-(1H-1,2,3,4-tetrazol-1-yl)phenyl]-4-methyl-1,3-thiazole-5-carboxylic acid
(B-25) 2-[4-(2,6-difluorophenoxy)-3-(1H-1,2,3,4-tetrazol-1-yl)phenyl]-4-methyl-1,3-thiazole-5-carboxylic acid
(B-26) 2-[4-(3-fluorophenoxy)-3-(1H-1,2,3,4-tetrazol-1-yl)phenyl]-4-methyl-1,3-thiazole-5-carboxylic acid
(B-27) 2-[4-(3-methylphenoxy)-3-(1H-1,2,3,4-tetrazol-1-yl)phenyl]-4-methyl-1,3-thiazole-5-carboxylic acid
(B-28) 2-[4-(2-chlorophenoxy)-3-(1H-1,2,3,4-tetrazol-1-yl)phenyl]-4-methyl-1,3-thiazole-5-carboxylic acid
(B-29) 2-[4-(4-fluoro-3-methylphenoxy)-3-(1H-1,2,3,4-tetrazol-1-yl)phenyl]-4-methyl-1,3-thiazole-5-carboxylic acid
(B-30) 2-[4-(4-fluoro-2-methylphenoxy)-3-(1H-1,2,3,4-tetrazol-1-yl)phenyl]-4-methyl-1,3-thiazole-5-carboxylic acid
(B-31) 2-[4-(2,4-difluorophenoxy)-3-(1H-1,2,3,4-tetrazol-1-yl)phenyl]-4-methyl-1,3-thiazole-5-carboxylic acid
(B-32) 2-[4-(2-fluoro-6-methoxyphenoxy)-3-(1H-1,2,3,4-tetrazol-1-yl)phenyl]-4-methyl-1,3-thiazole-5-carboxylic acid
(B-33) 2-[4-(2-methylphenoxy)-3-(1H-1,2,3,4-tetrazol-1-yl)phenyl]-4-methyl-1,3-thiazole-5-carboxylic acid
(B-34) 2-[4-(4-methylphenoxy)-3-(1H-1,2,3,4-tetrazol-1-yl)phenyl]-4-methyl-1,3-thiazole-5-carboxylic acid
(B-35) 2-[4-(3-fluoro-5-methylphenoxy)-3-(1H-1,2,3,4-tetrazol-1-yl)phenyl]-4-methyl-1,3-thiazole-5-carboxylic acid
(B-36) 2-[4-(2,5-difluorophenoxy)-3-(1H-1,2,3,4-tetrazol-1-yl)phenyl]-4-methyl-1,3-thiazole-5-carboxylic acid
(B-37) 2-[4-(2-fluoro-5-methylphenoxy)-3-(1H-1,2,3,4-tetrazol-1-yl)phenyl]-4-methyl-1,3-thiazole-5-carboxylic acid
(B-38) 4-methyl-2-{4-[(2-methylpropyl)sulfanyl]-3-(1H-1,2,3,4-tetrazol-1-yl)phenyl}-1,3-thiazole-5-carboxylic acid
(B-39) 4-methyl-2-[4-(propan-2-ylsulfanyl)-3-(1H-1,2,3,4-tetrazol-1-yl)phenyl]-1,3-thiazole-5-carboxylic acid
(B-40) 4-methyl-2-{4-[(4-methylphenyl)sulfanyl]-3-(1H-1,2,3,4-tetrazol-1-yl)phenyl}-1,3-thiazole-5-carboxylic acid
(B-41) 2-[4-(N,N-diethylamino)-3-(1H-1,2,3,4-tetrazol-1-yl)phenyl]-4-methyl-1,3-thiazole-5-carboxylic acid
(B-42) 4-methyl-2-[4-(pyrrolidine-1-yl)-3-(1H-1,2,3,4-tetrazol-1-yl)phenyl]-1,3-thiazole 5-carboxylic acid.

The compound represented by Formula (II) can be prepared by the well-known method including the method described in WO2014/119681.

When $R^{1b}$ is $OR^b$ or $SR^b$, $R^b$ is preferably a C1-C8 alkyl group optionally substituted with one or a plurality of C1-C8 alkoxy groups, halogen atoms or hydroxyl groups, an aryl group optionally substituted with one or a plurality of C1-C8 alkyl groups, C1-C8 alkoxy groups or halogen atoms, more preferably a C1-C8 alkyl group optionally substituted with one or a plurality of C1-C8 alkoxy groups or hydroxyl groups, most preferably an isopropyl group, an isobutyl group, and a neopentyl group.

In the case when $R^{1b}$ represents $NR^bR^{b'}$ which may form a ring, "$NR^bR^{b'}$ forms a ring" means that $R^b$ and $R^{b'}$ are taken together to form a nitrogen-containing saturated ring with nitrogen atom to which these are bound. The same applies to $NR^dR^{d'}$ in Formula (IV). When $R^{1b}$ represents $NR^bR^{b'}$ which may form a ring, $R^b$ and $R^{b'}$ preferably represent independently a C1-C8 alkyl group optionally substituted with a hydroxyl group, more preferably represent independently a methyl group, an ethyl group, an isopropyl groups, or are taken together to form a pyrrolidin-1-yl group, a piperidin-1-yl group, a morpholin-1-yl group with nitrogen atom to which these are bound.

$R^{2b}$ preferably represents a hydrogen atom or a C1-C3 alkyl group and specifically a methyl group, an ethyl group, an n-propyl group or an isopropyl group, more preferably a hydrogen atom or a methyl group, and particularly preferably a methyl group.

$X^{1b}$, $X^{2b}$ and $X^{3b}$ preferably represent independently $CR^{3b}$ or a nitrogen atom, more preferably a combination wherein $X^{1b}$ represents a nitrogen atom, and $X^{2b}$ represents $CR^{3b}$ or a nitrogen atom, and $X^{3b}$ represents $CR^{3b}$. $R^{3b}$ preferably represents a hydrogen atom in any of the combinations.

Combination of substituents in the above-mentioned Formula (II) is preferably a combination of groups selected from preferable groups, more preferably from more preferable groups, and further preferably from particularly preferable groups. The preferable combination of substituent is described in WO2014/119681.

Compounds represented by Formula (II) are preferably Compounds B-1 to B-42, and more preferably Compounds B-8, B-13, B-14 and B-15.

Examples of Formula (III)

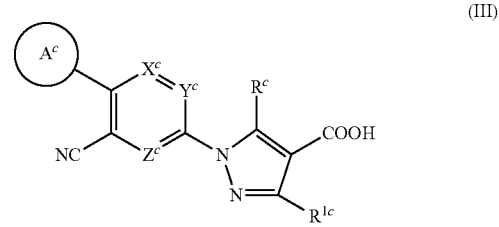

(III)

(wherein $A^c$ represents a C6-C10 aryl group of or a heteroaryl group, wherein the aryl or the heteroaryl group is unsubstituted or optionally substituted with 1 to 3 groups of $Q^c$, wherein the $Q^c$ is the same or different from each other, and is selected from the group consisting of halogen atom, —CN, —NO$_2$, C1-C6 alkyl group, C3-C7 cycloalkyl group, C1-C6 halogenoalkyl group, phenyl group, —CH$_2$—O—$R^{2c}$, —O—$R^{2c}$, —O—(C1-C6 halogenoalkyl), —O-benzyl, —O-phenyl, —O—CO—$R^{2c}$, —NR$^{3c}$R$^{4c}$, —NH—CO—$R^{2c}$, —CO$_2$—$R^{2c}$, —CO—$R^{2c}$, —CO—NR$^{3c}$R$^{4c}$, —NH—SO$_2$—$R^{2c}$, —CO-aryl, —S—$R^{2c}$, —SO$_2$—(C1-C6 alkyl) and —SO$_2$-phenyl.

$X^c$, $Y^c$ and $Z^c$ represent a $CR^{5c}$ or a nitrogen atom, wherein one of $X^c$, $Y^c$ and $Z^c$ is a nitrogen atom and other two are $CR^{5c}$.

$R^c$ represents a hydrogen atom or a C1-C6 alkyl group.

$R^{1c}$ represents a hydrogen atom, an amino group or a C1-C6 alkyl group.

$R^{2c}$ represents a hydrogen atom or a C1-C6 alkyl group.

$R^{3c}$ and $R^{4c}$ are the same or different from each other, and represent a hydrogen atom or a C1-C6 alkyl group, wherein $R^{3c}$ and $R^{4c}$ may be taken together to form a monocyclic nitrogen-containing saturated heterocycle to which the nitrogen atom is bound with $R^{3c}$ and $R^{4c}$.

$R^{5c}$ represents a hydrogen atom, a halogen atom or a C1-C6 alkyl group.), or pharmaceutically acceptable salts thereof in the present invention include the following compounds:

(C-1) 1-(4-cyano-5-phenylpyridin-2-yl)-1H-pyrazole-4-carboxylic acid (C-2) 1-[4-cyano-5-(2-fluorophenyl)pyridin-2-yl]-1H-pyrazole-4-carboxylic acid (C-3) 1-[4-cyano-5-(3-methylphenyl)pyridin-2-yl]-1H-pyrazole-4-carboxylic acid (C-4) 1-[4-cyano-5-(4-methylphenyl)pyridin-2-yl]-1H-pyrazole-4-carboxylic acid (C-5) 1-[4-cyano-5-(2-fluoro-3-methoxyphenyl)pyridin-2-yl]-1H-pyrazole-4-carboxylic acid (C-6) 1-[4-cyano-5-(thiophen-3-yl)pyridin-2-yl]-1H-pyrazole-4-carboxylic acid (C-7) 1-[4-cyano-5-(2-fluoro-4-methoxyphenyl)pyridin-2-yl]-1H-pyrazole-4-carboxylic acid.

The compound represented by Formula (III) can be prepared by the well-known method including the method described in WO2014/157740.

Examples of "aryl group" or "heteroaryl group" of $A^c$ preferably include phenyl group, pyridyl group, pyrazyl group, pyrimidyl group, furyl group, thienyl group, isoxazolyl group, isothiazolyl group, benzofuranyl group, benzothienyl group, benzothiazolyl group, benzimidazolyl group, benzoxazolyl group, pyranyl group, imidazolyl group, oxazolyl group, thiazolyl group, triazinyl group, triazolyl group, benzoxazolyl group, benzisoxazolyl group and the like, and a phenyl group, a thienyl group are more preferable.

$A^c$ is unsubstituted or optionally substituted with 1 to 3 groups of $Q^c$, wherein the $Q^c$ is the same or different from each other, and is selected from the group consisting of halogen atom, —CN, —NO$_2$, C1-C6 alkyl group, C3-C7 cycloalkyl group, C1-C6 halogenoalkyl group, phenyl group, —CH$_2$—O—$R^{2c}$, —O—$R^{2c}$, —O—(C1-C6 halogenoalkyl), —O-benzyl, —O-phenyl, —O—CO—$R^{2c}$, —NR$^{3c}$R$^{4c}$, —NH—CO—$R^{2c}$, —CO$_2$—$R^{2c}$, —CO—$R^{2c}$, —CO—NR$^{3c}$R$^{4c}$, —NH—SO$_2$—$R^{2c}$, —CO-aryl, —S—$R^{2c}$, —SO$_2$—(C1-C6 alkyl) and —SO$_2$-phenyl. When $A^c$ is substituted with $Q^c$, the number of $Q^c$ is preferably one or two. $A^c$ is preferably unsubstituted or optionally substituted with $Q^c$ which is selected from the group consisting of halogen atom, C1-C6 alkyl group, C3-C7 cycloalkyl group, C1-C6 halogenoalkyl group, phenyl group, —O—$R^{2c}$ and —O—(C1-C6 halogeno alkyl). $A^c$ is more preferably unsubstituted or optionally substituted with $Q^c$ which is selected from the group consisting of halogen atom, methyl group and methoxy group. A halogen atom is preferably a fluorine atom.

The particularly preferable examples of $A^c$ can be represented by the following structural formulas.

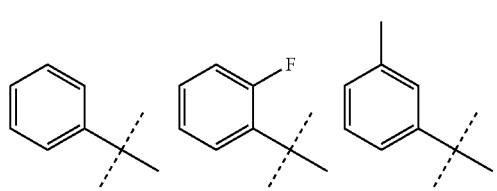

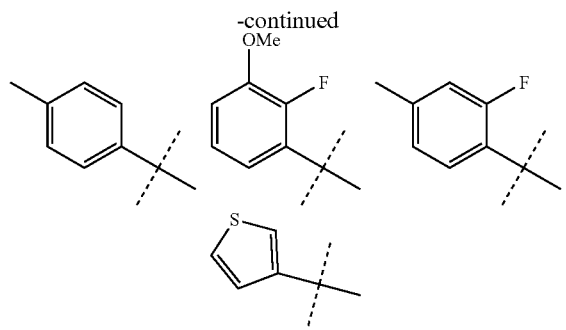

In the above Formula (III), $R^c$ represents a hydrogen atom or a C1-C6 alkyl group. "C1-C6 alkyl group" preferably include methyl group, ethyl group, n-propyl group, n-butyl group, n-pentyl group, n-hexyl group, isopropyl group, isobutyl group, s-butyl group, t-butyl group, isopentyl group, 2-methylbutyl group, neopentyl group, 1-ethylpropyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutylgroup, 2-ethylbutylgroup, t-pentyl group, isohexyl group and the like, $R^c$ is preferably a hydrogen atom or a methyl group, and particularly preferably a hydrogen atom.

In the above Formula (III), examples of "C1-C6 alkyl group" in $R^{1c}$ preferably include methyl group, ethyl group, n-propyl group, n-butyl group, n-pentyl group, n-hexyl group, isopropyl group, isobutyl group, s-butyl group, t-butyl group, isopentyl group, 2-methylbutyl group, neopentyl group, 1-ethylpropyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group, 2-ethylbutyl group, t-pentyl group, isohexyl group and the like, $R^{1c}$ is preferably a hydrogen atom, an amino group or a methyl group, and particularly preferably a hydrogen atom.

Examples of "C1-C6 alkyl group" in $R^{2c}$ preferably include methyl group, ethyl group, n-propyl group, n-butyl group, n-pentyl group, n-hexyl group, isopropyl group, isobutyl group, s-butyl group, t-butyl group, isopentyl group, 2-methylbutyl group, neopentyl group, 1-ethylpropyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutylgroup, 2-ethylbutylgroup, t-pentylgroup, isohexyl group and the like, $R^2$ is preferably a hydrogen atom or a methyl group, and particularly preferably a methyl group.

Examples of "C1-C6 alkyl group" in $R^{3c}$ and $R^{4c}$ preferably include methyl group, ethyl group, n-propyl group, n-butyl group, n-pentyl group, n-hexyl group, isopropyl group, isobutyl group, s-butyl group, t-butyl group, isopentyl group, 2-methylbutyl group, neopentyl group, 1-ethylpropyl group, 4-methyl pentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group, 2-ethylbutyl group, t-pentyl group, isohexyl group and the like, and examples of "monocyclic nitrogen-containing saturated heterocycle" preferably include pyrrolidine, piperidin, piperazin, azepane, diazepane, azocane, morpholine, thiomorpholine, tetrahydropyridine ring and the like. "Monocyclic nitrogen-containing saturated heterocycle," more preferably include hydrogen atom, methyl group, pyrrolidine, piperidin, piperazin and morpholine, and particularly preferably hydrogen atom, methyl group and morpholine.

$X^c$, $Y^c$ and $Z^c$ represent $CR^{5c}$ or a nitrogen atom, wherein one of $X^c$, $Y^c$ and $Z^c$ represents a nitrogen atom and other two represent $CR^{5c}$. When either of $X^c$, $Y^c$ or $Z^c$ is a nitrogen atom, $Y^c$ is preferably a nitrogen atom.

Examples of $R^{5c}$ include hydrogen atom, halogen atom or C1-C6 alkyl group, and a hydrogen atom is preferable.

Combination of substituent in the above-mentioned Formula (II) is preferably a combination of groups selected from preferable groups, more preferably from more preferable groups, and further preferably from particularly preferable groups. The preferable combination of substituents for the above-mentioned Formula (III) is described in WO2014/157740.

Examples of the compound represented by Formula (III) are preferably Compounds C-1 to C-7, and more preferably Compounds C-1, C-3 and C-4.

Examples of Azolecarboxylic Acid Compound Represented by Formula (IV)

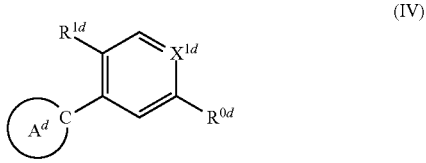

(wherein
$R^{0d}$ represents following $R^{01d}$ or $R^{02d}$.

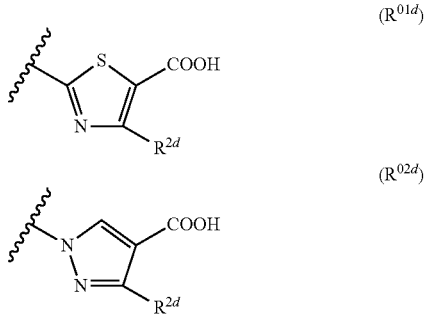

(wherein
$R^{1d}$ represents an aryl group optionally substituted with one or a plurality of C1-C6 alkyl groups, C1-C6 alkoxy groups or halogen atoms, $OR^d$, $NR^dR^{dh}$ optionally forming a ring or $SR^d$, wherein $R^d$ and $R^{dh}$ independently represent a hydrogen atom, a C1-C8 alkyl group optionally substituted with one or a plurality of C1-C8 alkoxy groups, halogen atoms, hydroxyl groups, an aryl group optionally substituted with one or a plurality of C1-C6 alkyl groups, C1-C6 alkoxy groups, halogen atoms or cyano groups, or a heteroaryl group optionally substituted with one or a plurality of C1-C6 alkyl groups, C1-C6 alkoxy groups or halogen atoms.)

$R^{2d}$ represents a hydrogen atom, an amino group or a C1-C8 alkyl group optionally substituted with one or a plurality of halogen atoms.

$X^{1d}$ represents $CR^3$ or a nitrogen atom, wherein $R^3$ represents a hydrogen atom or a halogen atom.

Ring $A^d$ represents a 5- or 6-membered monocyclic heteroarene optionally substituted with 1 to 4 groups selected from the group consisting of C1-C6 alkyl group optionally substituted with one or a plurality of C1-C3 alkoxy groups or halogen atoms, C1-C6 alkoxy group optionally substituted with one or a plurality of halogen atoms, and halogen atom.), or pharmaceutically acceptable salts thereof in the present invention include the following compounds:

(D-1) 2-(4-isobutoxy-3-thiazol-5-yl-phenyl)-4-methyl-1,3-thiazole-5-carboxylic acid
(D-2) 2-(4-isobutoxy-3-oxazol-5-yl-phenyl)-4-methyl-1,3-thiazole-5-carboxylic acid
(D-3) 2-[4-isobutoxy-3-(1-methyltetrazol-5-yl)-phenyl]-4-methyl-1,3-thiazole-5-carboxylic acid.

The compound represented by Formula (III) can be prepared by the well-known method including the method described in WO2016/017699.

In Formula (IV), $R^{1d}$ is preferably $OR^d$. When $R^{1d}$ is $OR^d$ or $SR^d$, $R^d$ is preferably a C1-C8 alkyl group optionally substituted with one or a plurality of C1-C8 alkoxy groups, halogen atoms or hydroxyl groups, or an aryl group optionally substituted with one or a plurality of C1-C6 alkyl groups, C1-C6 alkoxy groups, halogen atoms or cyano groups, more preferably a C1-C8 alkyl group optionally substituted with one or a plurality of C1-C8 alkoxy groups or halogen atoms, and particularly preferably an isopropyl group, an isobutyl group or a neopentyl group.

When $R^{1d}$ is an aryl group optionally substituted with one or a plurality of C1-C6 alkyl groups, C1-C6 alkoxy groups, halogen atoms or cyano groups, the aryl group is preferably an aryl group optionally substituted with one or a plurality of C1-C3 alkyl groups, C1-C3 alkoxy groups or halogen atoms, and more preferably a phenyl group optionally substituted with a fluorine atom.

$R^{2d}$ is preferably a hydrogen atom or a C1-C3 alkyl group and specifically includes methyl group, ethyl group, n-propyl group and isopropyl group, more preferably hydrogen atom and methyl group, and particularly preferably methyl group.

$R^{1d}$ and $R^{2d}$ are preferably as described above when R is either of $R^{01d}$ or $R^{02d}$. In addition, when $R^{01d}$ is $R^{02d}$, $R^{2d}$ preferably includes also amino group and C1-C3 alkyl group optionally substituted with one or a plurality of halogen atoms, and more preferably hydrogen atom and amino group.

$X^{1d}$ represents $CR^{3d}$ or nitrogen atom, and $R^{3d}$ represents a hydrogen atom or a halogen atom.

Ring $A^d$ binds with a benzene including $X^{1d}$ or a pyridine ring via a carbon atom in ring $A^d$. A 5- or 6-membered monocyclic heteroarene in ring $A^d$ includes the following structures:

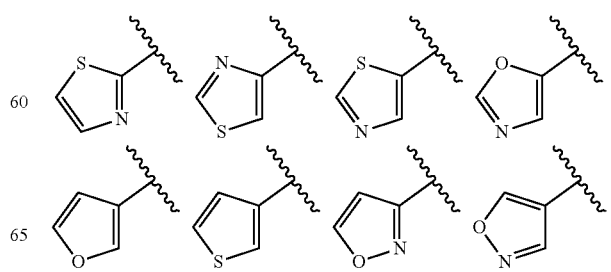

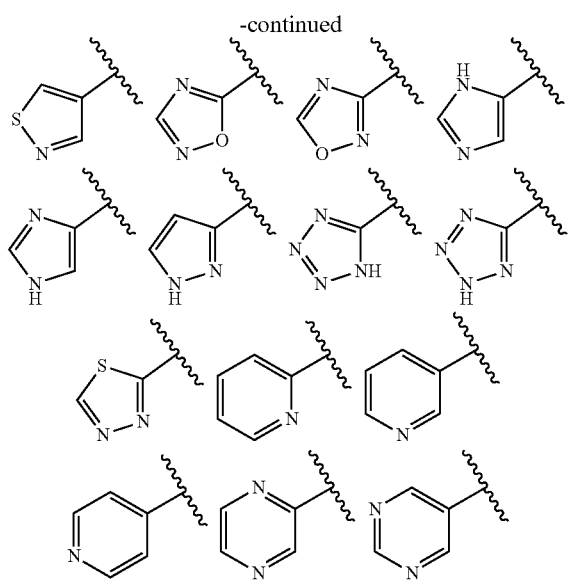

Ring $A^d$ preferably represents a 5- or 6-membered monocyclic heteroarene optionally substituted with one or two C1-C3 alkyl groups optionally substituted with one or two C1-C3 alkoxy groups, more preferably a 5- or 6-membered monocyclic heteroarene optionally substituted with one or two methyl groups. Specific examples of ring $A^d$ preferably are as follows:

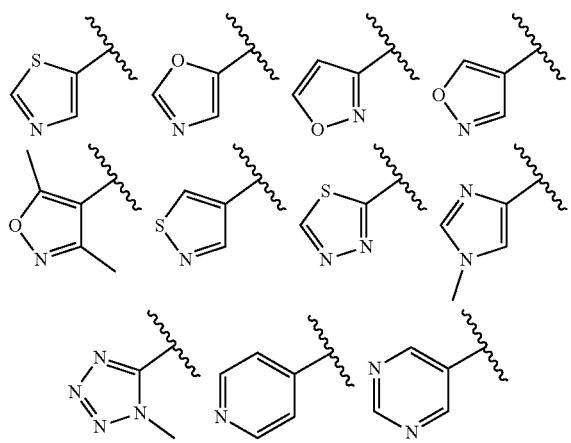

Combination of substituents in the above-mentioned Formula (IV) is preferably a combination of groups selected from preferable groups, more preferably from more preferable groups, and further preferably from particularly preferable groups. The preferable combination of substituents for the above-mentioned Formula (IV) is described in WO2016/017699.

Examples of the compound represented by Formula (IV) are preferably Compounds D-1, D-2 and D-3.

Dementia in this invention is defined as a disease which is diagnosed as dementia according to the International Classification of Diseases 10th Revision (ICD-10) published by the World Health Organization, the Diagnostic and Statistical Manual of Mental Disorders Third Edition (DSM-III-R) by the American Psychiatric Association, and a text version of the fourth edition (DSM-IV-TR) and those revised editions, and includes Alzheimer's dementia, dementia with Lewy bodies, frontotemporal dementia, cerebrovascular dementia, juvenile dementia, and Parkinson's disease.

In the present invention, the term "prophylactic" means to prevent incidence or onset of diseases in an individual who is not affected by diseases or has not yet developed diseases and the term "therapeutic" means to treat, suppress or remedy diseases or symptoms in an individual who has already been affected by diseases or has developed diseases.

The compounds represented by the above Formulas (I), (II), (III) and (IV) can be converted into a pharmaceutically acceptable salt as needed. Examples of such salts include salts with inorganic acids such as hydrochloric acid, hydrobromic acid, hydroiodic acid, sulfuric acid, nitric acid, phosphoric acid and carbonic acid; salts with organic acids such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid and p-toluenesulfonic acid; salts with amino acids such as lysin, arginine, ornithine, glutamine acid and aspartic acid; salts with alkali metals such as sodium, potassium and lithium; salts with alkaline earth metals such as calcium and magnesium; salts with metals such as aluminum, zinc and iron; salts with organic bases such as methylamine, ethylamine, t-octylamine, diethylamine, trimethylamine, triethylamine, ethylenediamine, piperidin, piperazin, pyridine, picoline, ethanolamine, diethanolamine, triethanolamine, cyclohexylamine, dicyclohexylamine, N-methylglucamine, tris(hydroxymethyl)aminomethane, N,N'-dibenzylethylenediamine; and ammonium salt and the like.

An active ingredient of the present invention can be used in any formulation such as solid preparation, semi-solid preparation and liquid preparation, or any application such as oral and non-oral preparations (parenteral injection, percutaneous absorption agents, eye drops, suppositories, nasal absorption agents, inhalation and the like).

Therapeutic agents or prophylactic agents for dementia such as AD containing a compound of the present invention or a pharmaceutically acceptable salt thereof as an active ingredient are generally prepared using carriers and diluting agents, and other additives which are used for conventional formulations. For carriers and diluting agents for the preparations, either a solid or liquid can be used, and include, for example, lactose, magnesium stearate, starch, talc, gelatin, agar, pectin, gum Arabic, olive oil, sesame oil, cocoa butter, ethylene glycol and other commonly used compounds. For administration, either oral administration with tablet, pill, capsule, granule, powder, liquid and the like, or parenteral administration, such as injection (IV infusion, intramuscular injection and the like), suppositories, percutaneous absorption agents and the like, may be adopted.

The dosage of the active ingredient in the present invention is an effective amount for the treatment or prevention of dementia such as AD, and can be determined depending on symptoms, age, body weight of patients, types of the combination therapy, frequency of treatment, and the types of expected effect or administration methods. The administration may be carried out every day or intermittently, the frequency of administration is 1 to 3 times/day, and dose per adult is usually about 0.5-1000 mg/time, (preferably 10-120 mg) and 0.5-3000 mg/day (preferably 10-360 mg, more preferably 10-120 mg). Also, the frequency of administration may be 1-3 times/week. In this case, the dose is usually about 0.5-1000 mg/time per adult. The formulations are preferably prepared to satisfy these conditions.

EXAMPLES

The present invention will be explained by examples in more details as follows, but the scope of the invention is not limited to the following examples.

Example 1

Inhibitory effect of Alzheimer's disease progress by 2-(3-cyano-4-isobutyloxyphenyl)-4-methyl-5-thiazolecarboxylic acid (Compound A)
1. Materials and Method
2-(3-Cyano-4-isobutyl oxyphenyl)-4-methyl-5-thiazole carboxylic acid (Compound A) was used as a compound which strongly inhibits the activity of xanthine oxidase.

The adjustment of concentrations of compound A and the given dose/the administration method of compound A followed the description below.

As a base, 0.5% methyl cellulose was prepared. When dissolving compound A in 0.5% of methyl cellulose as a solvent, first a stock solution that has a concentration by a factor of 10 (a 10-fold concentration stock solution) was made for the preparation for administrating compound A in order to avoid an error in the measurement of a minute amount of drugs and a decrease in their efficacies. In other words, after having ground compound A with a mortar made of agate, a small amount of 0.5% methyl cellulose was added to the compound A to obtain a suspension. Subsequently, a small amount of 0.5% methyl cellulose was again added gradually to the suspension and the mixture was completely suspended/dissolved. Finally, to 10 mL of 0.5% methyl cellulose, 50 mg of compound A was suspended/dissolved, thus a stock solution having 10-fold concentration of 50 mg of compound A in 10 mL of 0.5% methyl cellulose (50 mg/10 mL) was prepared. A stock solution having 10-fold concentration [50 mg of compound A/10 mL of 0.5% methyl cellulose (50 mg/10 mL)] was prepared every week and stored under refrigeration. The stock solution having 10-fold concentration was diluted by a factor of 10 while stirring fully on the day of administration. When administering to mice, the drug as agitated was aspirated by a feeding tube to fulfill the given dose.

According to the above-mentioned method, namely for the final concentration of the administration, a test solution of 5 mg of compound A suspended/dissolved in a 10 mL solution of 0.5% methyl cellulose, namely, 5 mg of compound A/10 mL of 0.5% methyl cellulose (5 mg/10 mL) was prepared and the preparation equivalent to 5 mg of compound A per kg mouse body weight (5 mg/kg) was orally administered to the mouse once a day.

As a placebo, only a solvent of a 10 mL solution of 0.5% methyl cellulose per kg mouse body weight (10 mL/kg), namely the same amount of the solvent equivalent to the volume of the preparation administered to the mouse was orally administered once a day.

For the method of oral administration, the desired volume was exactly measured with a plastic syringe and the feeding tube was directly connected to the syringe to ensure the oral and transesophageal administration to mice.

As an experimental model for Alzheimer, an Alzheimer's disease double transgenic mouse model, a strain of Tg (APPSWE) 2576KhaTg (Prnp-MAPT*P301L) JNPL3HImc (TaconicFarms, Inc.) highly expressing both a gene with the genetic Sweden mutation coding 695 amino acids of amyloid β precursor protein of human Alzheimer's disease and a mutated gene in which 301st proline of human tau protein gene was mutated to leucine (P301L) was used. Mice of the Alzheimer's disease double transgenic mouse model were bred under SPF (specific pathogen free: the microbial controlled state without any specific pathogens) and they remained viable for approximately two years.

Mice of the Alzheimer's disease double transgenic mouse model were isolated individually for 4 weeks after the purchase in order to remove any infections that could happen due to the long experimental period in mice which might carry microorganisms and to minimize individual differences as much as possible. It was confirmed that mice were still SPF. Ten male mice were divided into two groups of five consisting of a compound A administration group (n=5) and a methyl cellulose administration group as a control group (n=5).

The appearance of senile plaques (SP) and neurofibrillary tangles (Neurofibrillary Tangle), which are hallmarks of histopathological images of human Alzheimer's disease, are recognized in this mouse model of one-year old (365 days old) or older as a natural development. However, senile plaques and neurofibrillary tangles are not confirmed in brains of normal 2 year-old mice. According to this finding and neuropathological findings of human Alzheimer's disease, it was concluded that these mice should have developed a condition equivalent to human Alzheimer's disease at the age of one. Based on this conclusion and in consideration of the clinical application to humans, the drug administration was started with this mouse model at the age of one (after the onset of Alzheimer's disease), when senile plaques and neurofibrillary tangles should appear as hallmarks of the histopathological images of Alzheimer's disease.

The condition of the mice was observed until they became one year old. After becoming one year old, the compound A administration group (n=5) had oral administration of 5 mg/kg of compound A using a feeding tube each day. The 0.5% methyl cellulose administration control group (n=5) had oral administration of only a 10 mL solution of 0.5% methyl cellulose per 1 kg mouse body weight (10 mL/kg) using a feeding tube every day (FIG. 1).

One mouse in the 0.5% methyl cellulose administration control group died suddenly when 690 days old. Five mice in the compound A administration group and four in the 0.5% methyl cellulose administration control group survived more than 690 days, so total nine experimental animals were adopted.

At 690-700 days after birth, the sampling method of the organ tissues of the total nine individuals including the five mice of compound A administration group and four mice of the control group was performed as follows.

To the nine mice, 1 mL of pentobarbital sodium (trade name: Nembutal, Dainippon Sumitomo Pharma Co., Ltd.) was intraperitoneally injected per 1 g body weight, thus carrying out general anesthesia. After confirming that mice were completely anesthetized, each individual under anesthesia was sacrificed humanely with a treatment of carbon dioxide, and laparotomy and thoracotomy were performed. After drawing blood from the right ventricle, the blood was removed from all the organs of the whole body with a perfusion of saline via the aorta of the left ventricle. Immediately thereafter, each fresh organ of a part of the right cerebral frontal lobe, a part of spinal cord, a part of the right and left ventricles of the heart, a part of the right lung, a part of the liver, a part of both kidneys, and the left testis were removed and flash frozen with dry ice. Subsequently, each fresh organs and serum were stored in a deep freezer at −80°

C. Simultaneously, as a procedure paralleled to the flash freezing of each fresh organ, the rest part of the organs except the part obtained as each fresh organ and all the other organs were infiltrated and fixed with 4% paraformaldehyde/ 0.1 M cacodylate buffer (pH 7.3).

All the organs such as cerebrum, cerebellum, brainstem and the spinal cord were embedded in paraffin and thinly sliced with a microtome. The treatment of organ tissues was carried out by the following six steps including a fixation of organ tissues, dehydration, ethanol removal, paraffin infiltration, paraffin embedding and preparation of paraffin sections.

(1) For the fixation of organ tissues, each tissue was infiltrated and fixed with 4% paraformaldehyde/0.1 M cacodylate buffer (pH 7.3).

(2) For the dehydration of organ tissues, the tissues were washed with a phosphate buffered saline (Phosphate buffered saline: PBS) three times. Subsequently, the organ tissues were washed with running tap water overnight, the tissues were infiltrated with 70% ethanol for 12 hours at room temperature, 80% ethanol for 12 hours at room temperature, 90% ethanol for 12 hours at room temperature, 99.5% ethanol for 12 hours at room temperature, 99.5% ethanol for 12 hours once more at room temperature, 100% of ethanol for 12 hours at room temperature and absolute ethanol for 12 hours at room temperature to completely replace the water in the organ tissues with ethanol.

(3) The organ tissues were replaced with chloroform to remove ethanol used for the dehydration. The replacement with chloroform was carried out three times by infiltration of the organ tissues in a chloroform tank for two hours at room temperature.

(4) The paraffin infiltration process of the organ tissues was carried out by placing an organ tissue in a paraffin tank at 60° C. from the chloroform tank.

(5) Chloroform was completely removed by infiltrating four times the organ tissues in the 60° C. paraffin tank for two hours to ensure complete infiltration of paraffin into the organ tissues. The organ tissues were then embedded in paraffin used for embedding.

(6) For the preparation of the paraffin section, a paraffin block of the paraffin embedded organ tissue was sliced at 6 m in thickness using a microtome.

For the purpose of evaluating the validity of murine cerebral nerve histopathological images, particularly neuropathological and histological images of senile plaques and neurofibrillary tangle, cerebral paraffin blocks prepared from four autopsy cases with Alzheimer's disease confirmed clinically by neuropathological diagnosis were used.

Observation of the murine cerebrum from the bottom of the brain confirmed the presence of a mammillary body. A carbon steel double-edged blade (FA-10, FEATHER Safety Razor) was cut at the center, and the double-edged blade was made into two single-edged blades. Using the carbon steel single-edged blade prepared in this way, the first coronal section was made in the center of the paraffin block of the murine cerebral mammillary body of the Alzheimer's disease double transgenic mouse model.

A cerebrum was sequentially cut from this mammillary body coronal sectioned surface in a thickness of 2 mm in the rostral and the caudal directions. At the site of the brainstem cerebellum, the first cut surface was prepared on a sectioned plane surface which included right and left trigeminal nerves of the pons and was positioned at the orthogonal angle to the longitudinal axis of the brain stem. The brainstem and cerebellum sectioned surface was sequentially cut at a thickness of 2 mm in both the rostral and the caudal directions, in a similar procedure to the preparation of the cerebrum sections.

The histochemical and immunohistochemical staining were carried out by the following methods.

(1) Prior to the histochemical and immunohistochemical staining of the paraffin sections, the following deparaffinization and rehydration were carried out. For the deparaffinization procedure, paraffin sections were immersed four times in a xylene tank for 5 minutes. Next, for the rehydration procedure, the deparaffinized section was immersed in a 100% ethanol tank for 5 minutes (twice), in a 95% ethanol tank for 5 minutes (once), in a 90% ethanol tank for 5 minutes (once) and in an 80% ethanol tank for 5 minutes- (once). Subsequently, the sections were washed with running tap water for 5 minutes.

(2) Hematoxylin and eosin (hematoxylin and eosin: HE) staining was carried out for histochemical staining. After the HE staining, the sections were subjected to each step of dehydration, infiltration and mounting. At first a dehydration step was carried out in the following conditions: 50% ethanol for 1 minutes (once), 70% ethanol for 1 minute (once), 80% ethanol for one minute (once), 90% ethanol for one minute (once), 95% ethanol for one minute (once), 100% ethanol for five minutes (once) and absolute ethanol for 5 minutes (once). The infiltration step was carried out by immersing-4 times the sections in xylene for 5 minutes. The mounting step was carried out by dropping a small amount of mounting medium (New M, X; Matsunami Glass Ind., Ltd.) onto a cover glass and covering the organ tissue specimens without inclusion of air.

(3) Regarding immunohistochemical staining, the detection of an amyloid β protein (Aβ), which is the core protein of a senile plaque, or a phosphorylated tau protein, which is the core protein of a neurofibrillary tangle, was carried out according to the following method.

1) Detection Method of an Amyloid β Protein

An amyloid β protein immunohistochemical staining kit (CodeNo. 299-56701 Wako Pure Chemical Industries) was used. For the detection of Aβ40 in the paraffin section, an anti-amyloid β protein (1-40) mouse monoclonal antibody (clonal No. BA27) in the kit was used. For the detection of Aβ42, an anti-amyloid β-protein (1-42) mouse monoclonal antibody (clonal No. BC05) in the kit was used. Finally, 3,3'-diaminobenzidine tetrahydrochloride (DAB; Dako) was used as a color developer for visualization.

2) Detection of a Phosphorylated Tau Protein:

A combination of the following primary antibody and ABC (avidin-biotin-immunoperoxidase complex) method was used to detect phosphorylated tau protein.

For primary antibody, an anti-phosphorylated tau protein (phosphorylated tau protein, PHF-tau) mouse monoclonal antibody (clone: AT8, Innogenetics (currently Fuji Rebio (Fujirebio)) was used. A Vectastain ABC Kit (Vector Laboratories) was used as an ABC kit.

Finally, DAB was used as a color developer for visualization. For the mounting process, tissue sections were embedded with a mounting medium in a similar manner to the HE staining.

Each stained specimen of HE staining, Aβ40 immunostaining, Aβ42 immunostaining, and AT8 immunostaining, was subjected to observation by using a light microscope (BX41: Olympus) equipped with a 3CCD digital camera system (FX380: Olympus) with image analysis software (FLVFS-LSVer. 1.12; Olympus) mounted after drying the mounting medium. The image analysis was carried out as well as the photography.

Figure 2:
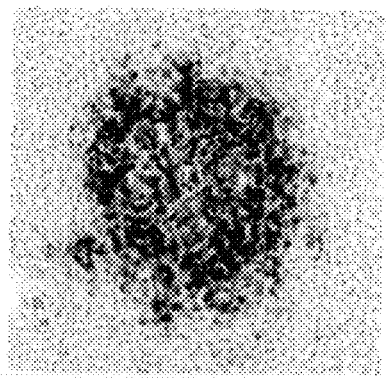
FIG. 2 shows histopathological images of the central nervous system of a patient with human Alzheimer's disease and of a mouse model with Alzheimer's disease.
Figure 2:
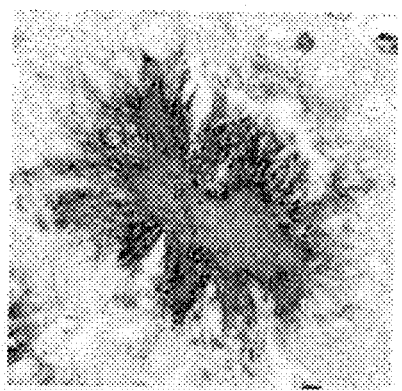
Figure 2:
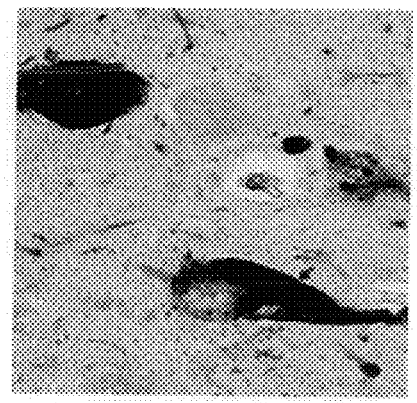
Figure 2:
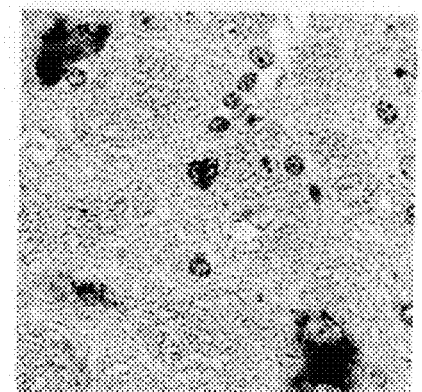

As a pilot study, ten male mice were used to demonstrate that the clinical condition of the Alzheimer's disease double transgenic mouse model was neuropathologically the same as in human Alzheimer's disease. From the immunohistochemical analysis, it was found that the neuropathological diagnostic hallmarks of human Alzheimer's disease, namely amyloid senile plaques for which Aβ40 and Aβ42 are core proteins and neurofibril for which a phosphorylated tau protein is a core protein, appeared frequently in mice of 690 days or older in the Alzheimer's disease double transgenic mouse model. While no such appearance was recognized in the age-matched normal mice. Regarding the senile plaques of the Alzheimer's disease double transgenic mouse model, their structures could be easily recognized in a similar manner to the identification of senile plaques of human Alzheimer's disease using only HE staining, which was routinely carried out. Senile plaques and neurofibrillary tangles appearing in the Alzheimer's disease double transgenic mouse model and senile plaques and the neurofibrillary tangles, the neuropathological and histological hallmarks of human Alzheimer's disease, were of the same structures neuropathologically (FIG. 2).

Figure 3:
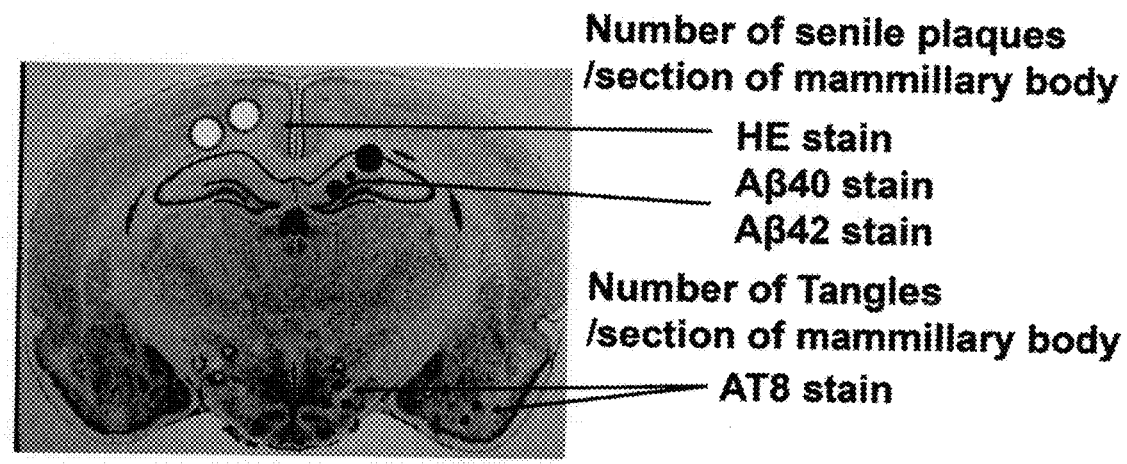
FIG. 3 shows common sites of senile plaques and a neurofibrillary tangle in a mouse model with Alzheimer's disease and a method to evaluate the effects of treatment.

In the Alzheimer's disease double transgenic mouse model, the common sites of the amyloid senile plaques for which Aβ40 and Aβ42 are the core proteins identified by immunostaining and senile plaques identified by HE staining were hippocampus (Ammon's horn), subiculum of hippocampus and cerebral cortex (particularly entorhinal cortex). The common sites of neurofibrillary tangles for which a phosphorylated tau protein is the core protein were the hypothalamic and amygdaloid nucleus. Based on this pilot study of the neuropathological analysis, as a method to evaluate the drugs' therapeutic effects, histochemical and immunohistochemical analysis was conducted quantitatively focusing on common sites of senile plaques and neurofibrillary tangles, that are the neuropathological and histological hallmarks of human Alzheimer's disease, in a cerebrum sectioned surface and brainstem/cerebellum sectioned surface in the Alzheimer's disease double transgenic mouse model (FIG. 3).

For therapeutic evaluation for Alzheimer's disease, with respect to the senile plaque and the neurofibrillary tangles, that are the neuropathological and histological hallmarks of human Alzheimer's disease, reductions of the number of occurrences of the former and of the number of the nerve cells with the latter in mice were quantitatively analyzed according to the following method and the results were evaluated.

Figure 4:
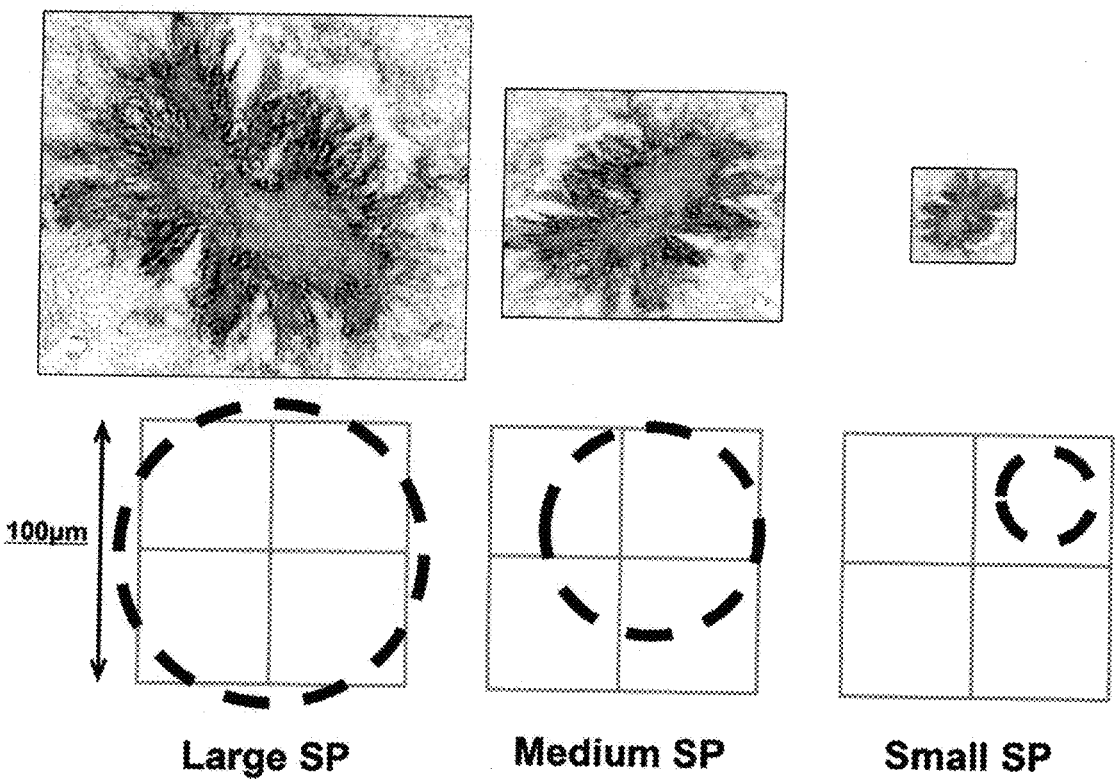
FIG. 4 shows an evaluation method of the size of senile plaques.
Figure 5:
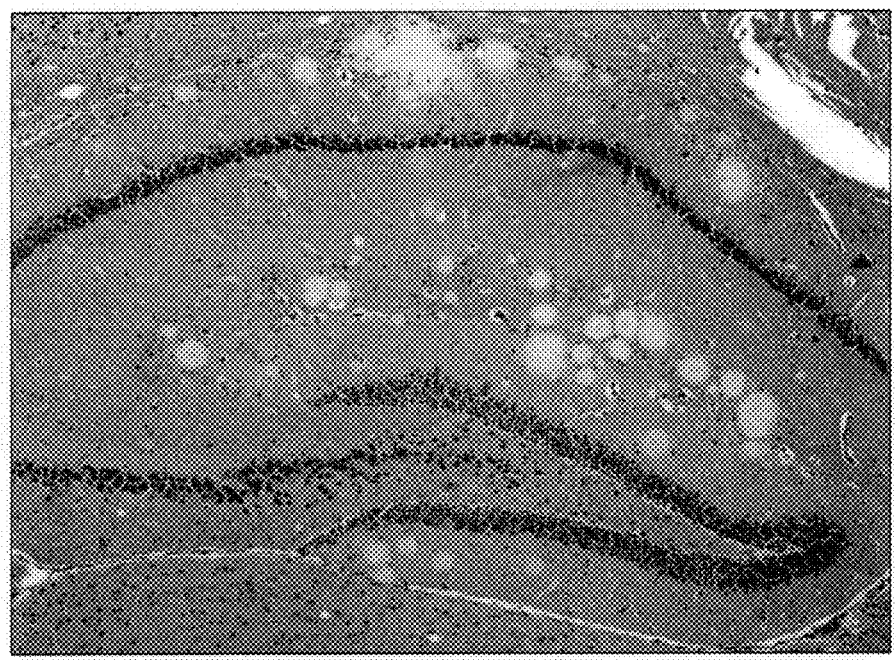
FIG. 5 shows the results of hematoxylin and eosin staining of the histopathological specimen of the mammillary body coronal section including the hippocampus of individuals in a control group administered with a placebo.
Figure 6:
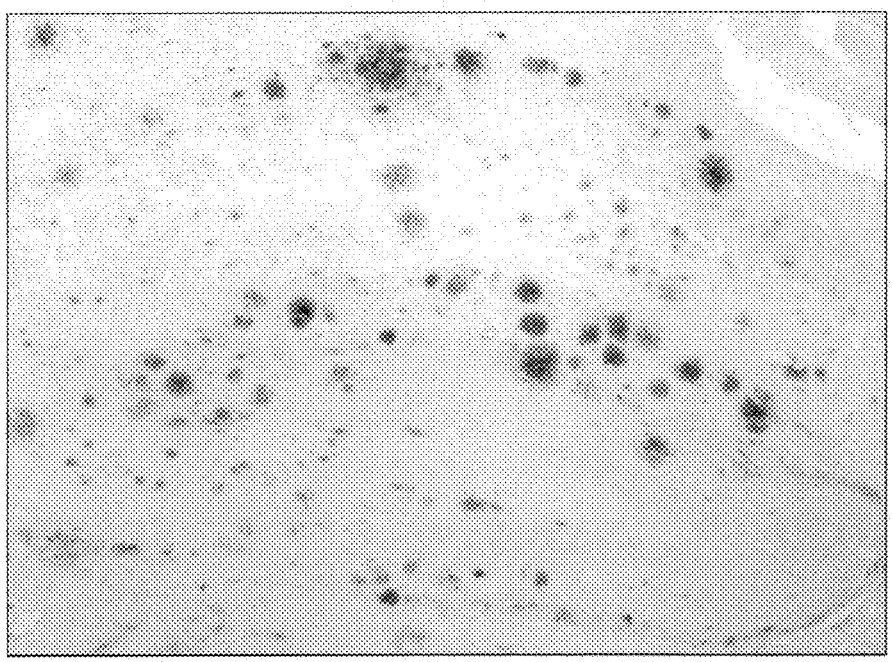
FIG. 6 shows the results of Aβ42 staining of the histopathological specimen of the mammillary body coronal section including the hippocampus of individuals in a control group administered with a placebo.
Figure 7:
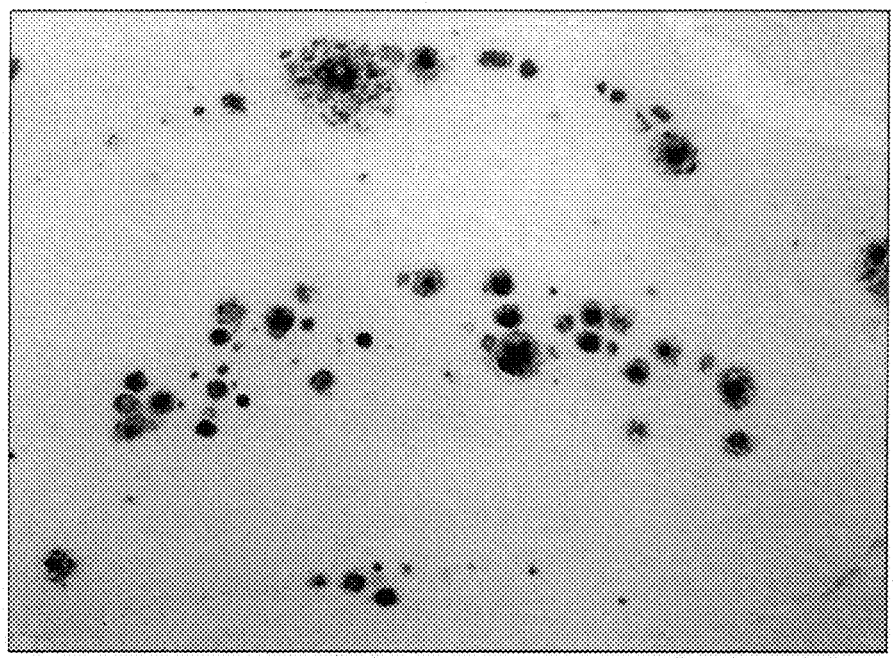
FIG. 7 shows the results of Aβ40 staining of the histopathological specimen of the mammillary body coronal section including hippocampus of individuals in a control group administered with a placebo.
Figure 8:
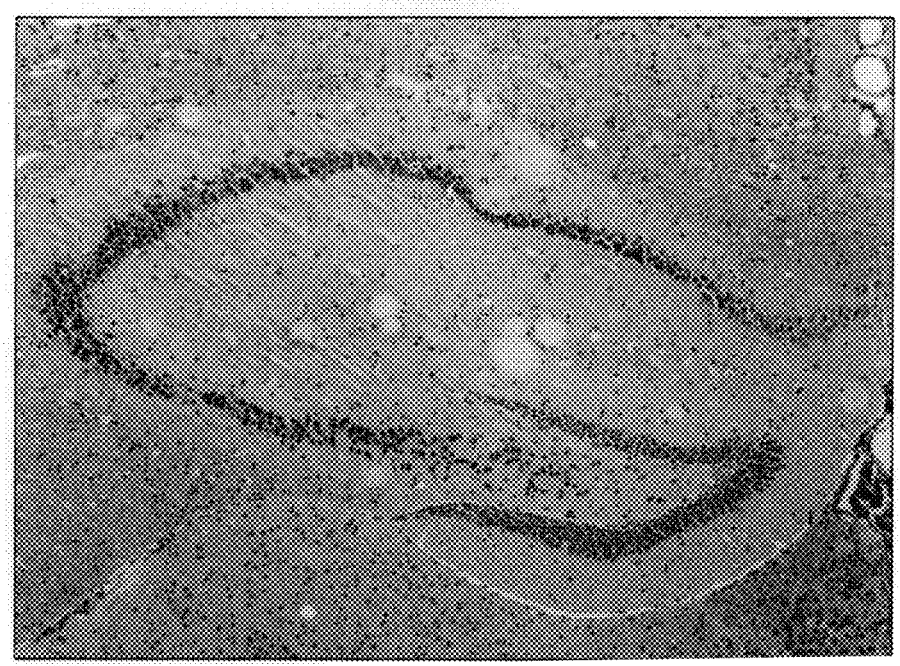
FIG. 8 shows the results of hematoxylin and eosin staining of the histopathological specimen of the mammillary body coronal section including hippocampus of individuals in a compound A administration group.
Figure 9:
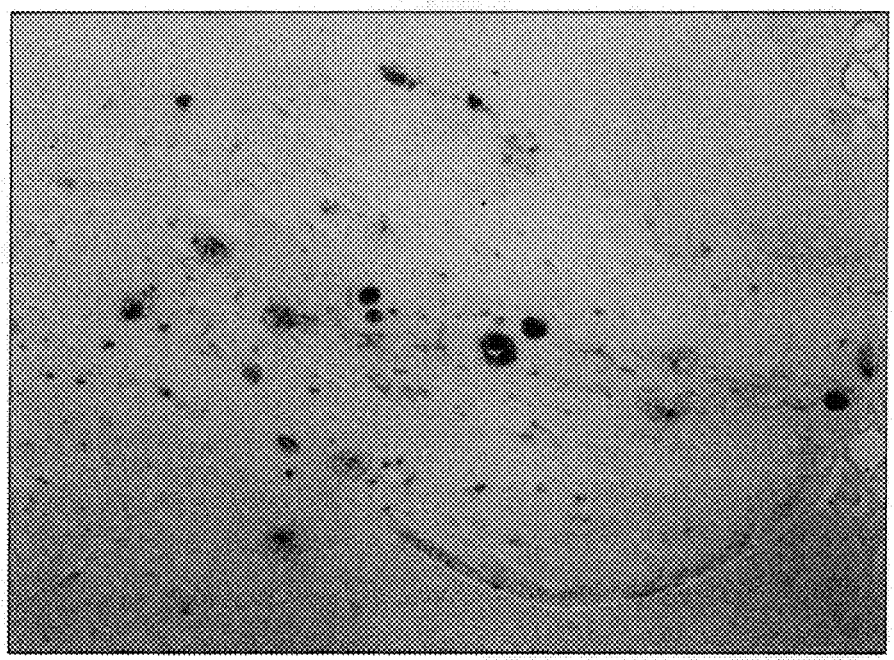
FIG. 9 shows the results of Aβ42 staining of the histopathological specimen of the mammillary body coronal section including hippocampus of individuals in a compound A administration group.
Figure 10:
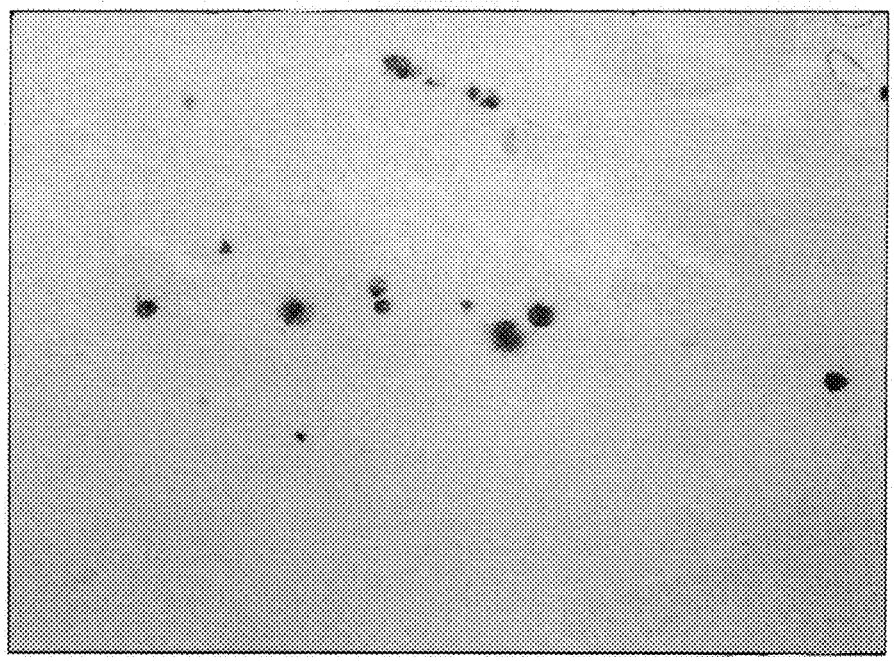
FIG. 10 shows the results of Aβ40 staining of the histopathological specimen of the mammillary body coronal section including hippocampus of individuals in a compound A administration group.

Senile plaques were searched in regard to two elements: the number and the size of the senile plaques (the growth degree of senile plaques). In other words, the individual senile plaques were divided into three groups: large senile plaques with a diameter of 100 μm or more; small senile plaques with a diameter of 50 μm or less; and medium senile plaques with a diameter of the 50 μm to 100 m. And then, the number of senile plaques was counted for each of these groups (FIG. 4). When the numbers were counted, a double-blind test was carried out. In other words, in neuropathological quantitative analysis, the specimens were marked only by simple individual ID numbers and the counts in the specimens were measured under the condition whereby the specimens were not identified as to whether they were from the placebo administration group or from the compound A administration group.

Neurofibrillary tangle was evaluated only by counting nerve cells with neurofibrillary tangles. Regarding counting the numbers, a double-blinded test was carried out in a similar way to the measurement of the senile plaques.

The quantitative values of the frequency of appearance of senile plaques and the number of nerve cells accompanying the neurofibrillary tangles were shown as mean±standard deviation. Statistical analysis of the study was carried out using Statview (Ver. 5.0, SAS Institute Inc.) software. A significance test was performed using a Mann-Whitney U test or a Kruskal-Wallis test and statistical significance was judged at hazard ratio $P<0.05$.

2. Results (1) Senile Plaques

1) Neuropathological and Morphological Characteristics of Senile Plaques

FIG. 5, FIG. 6, FIG. 7, FIG. 8, FIG. 9 and FIG. 10 illustrate histopathological specimens of the mammillary body coronal section including the hippocampus in the cerebrum of the Alzheimer's disease double transgenic mouse model. Senile plaques were able to be easily identified by HE staining in the hippocampus of the Alzheimer's disease double transgenic mouse model, while senile plaques did not appear in normal mice younger than 690 days nor in normal mice 690 days old or older. Senile plaques appearing in the Alzheimer's disease double transgenic mouse model had two types of neuropathological and morphological characteristics. One consisted of a center region stained densely by HE staining referred to as core and the structure of the periphery faintly stained by HE staining (halo). The other type had only a halo faintly stained by HE staining. According to HE staining, senile plaques appearing in the mice were the same as those appearing in human Alzheimer's disease. Among the senile plaques which appeared in the Alzheimer's disease double transgenic mouse model, the former senile plaque recognized in HE staining was equivalent to a classical-type senile plaque which appears in human Alzheimer's disease. And the latter senile plaque was equivalent to a diffuse-type senile plaque which appears in human Alzheimer's disease.

The senile plaques identified by HE staining which appeared in the Alzheimer's disease double transgenic mouse model were able to be identified by either anti-Aβ40 antibody or anti-Aβ42 antibody or by both antibodies. Senile plaques appearing in the 0.5% methyl cellulose administration control group (FIG. 5, FIG. 6 and FIG. 7) and compound A administration group (FIG. 8, FIG. 9 and FIG. 10) are the same neuropathologically, morphologically and immunohistochemically. Also, Aβ40/Aβ42 immunostaining-positive senile plaques which appeared in both administration groups in the Alzheimer's disease double transgenic mouse model, are neuropathologically, morphologically and immunohistochemically the same as Aβ40/Aβ42 immunostaining-positive senile plaques appearing in human Alzheimer's disease.

2) Result of Quantitative Analysis of the Number of the Senile Plaques

Because neuropathological and histological characteristics of senile plaques in the Alzheimer's disease double transgenic mouse model were the same as those in human Alzheimer's disease, and the neuropathological and histological characteristics of senile plaques in the control group and compound A administration group were the same, the inhibitory efficacy of human Alzheimer's disease by compound A was evaluated by quantitative analysis of the count of senile plaques and its diameter (the degree of growth) in terms of senile plaques. In consideration of the common sites for senile plaques in the Alzheimer's disease double transgenic mouse model, senile plaques which appeared in the mammillary body coronal section (including hippocampus and subiculum) and an entorhinal cortex coronal section (cerebral cortex including hippocampus, subiculum and entorhinal cortex) were counted by triple sequential staining of HE staining, Aβ40 immunostaining and Aβ42 immunostaining.

Figure 11:
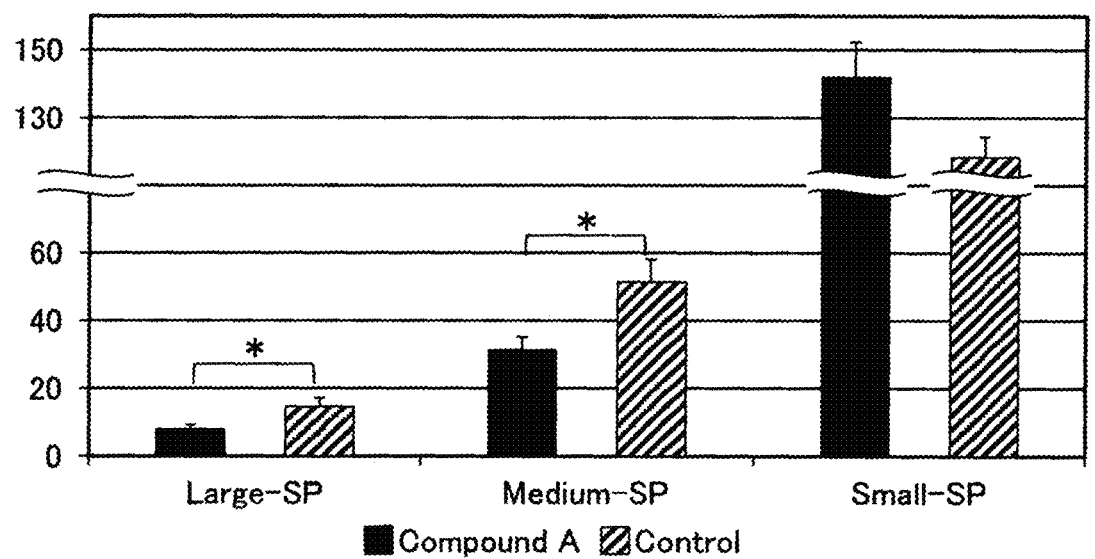
FIG. 11 shows the number of the senile plaques in the compound A administration group and in the control group.
Figure 12:
FIG. 12 shows the results of the hematoxylin and eosin staining of histopathological specimen of cerebrum sectioned at a coronal section including an amygdaloid nucleus and hypothalamus in an individual cerebrum of the control group administered with a placebo.
Figure 13:
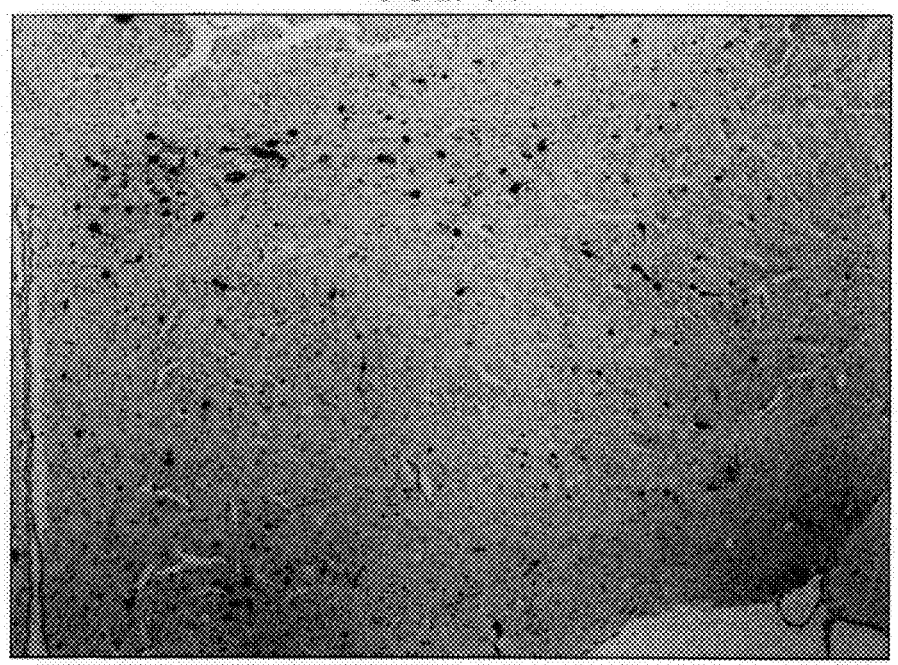
FIG. 13 shows the results of the AT8 immunostaining of histopathological specimen of cerebrum sectioned at a coronal section including an amygdaloid nucleus and hypothalamus in the individual cerebrum of the control group administered with a placebo.
Figure 14:
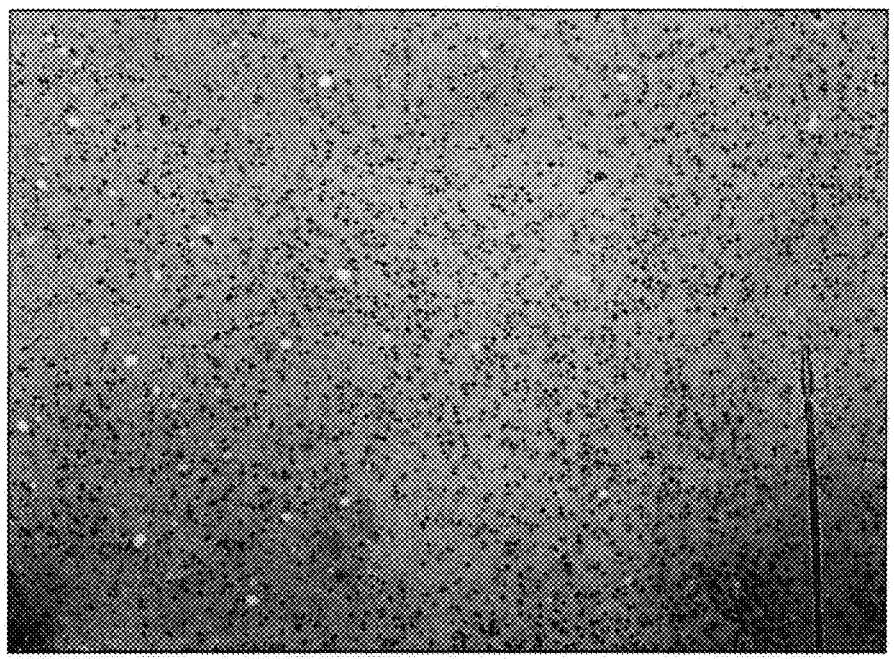
FIG. 14 shows the results of the hematoxylin and eosin staining of the histopathological specimen of cerebrum sectioned at a coronal section including an amygdaloid nucleus and hypothalamus in individual cerebrum of the compound A administration group.
Figure 15:
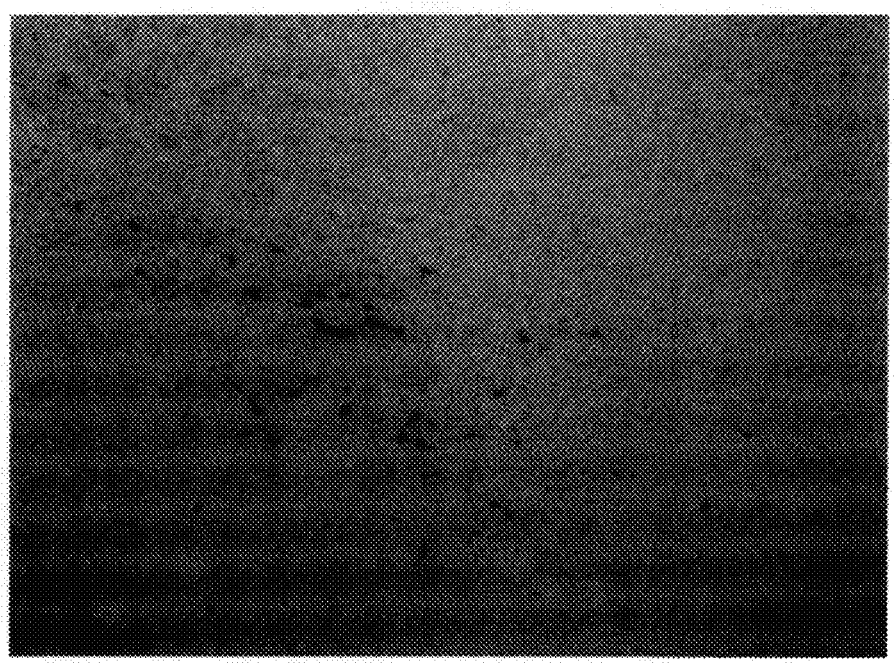
FIG. 15 shows the results of the AT8 immunostaining of the histopathological specimen of cerebrum sectioned at a coronal section including an amygdaloid nucleus and hypothalamus in individual cerebrum of the compound A administration group.

The mean±standard error of the number of large senile plaques in the cerebrum 1 coronal section was expressed as 7.9±1.3 for the compound A administration group and 14.5±2.6 for the control group. The number of the medium senile plaques was 31.2±3.9 for the compound A administration group and 51.4±6.8 for the control group. And the number of the small senile plaques was 148.5±13.2 for the compound A group and 112.0±8.0 for the control group (FIG. 11).

As a result of the statistical analysis, in the comparison between the number of large senile plaques and the number of medium senile plaques, compound A administration group showed significant decrease compared to the number of the senile plaques in the control group (p=0.033, p=0.006, Mann-Whitney U test). There was no significant difference in the number of small senile plaques in the two groups (p=0.055, Mann-Whitney U test) (FIG. 11).

(2) Neurofibrillary Tangle

1) Neuropathological and Morphological Characteristics of the Neurofibrillary Tangle Histopathological specimens of the coronal section of the cerebrum including an amygdaloid nucleus and the hypothalamus in the cerebrum of the Alzheimer's disease double transgenic mouse model are shown in FIG. 12, FIG. 13, FIG. 14 and FIG. 15.

In the hypothalamus and the amygdaloid nucleus of Alzheimer's disease double transgenic mouse model, neurofibrillary tangles, which don't appear in normal mice 700 days old or younger nor in normal mice over 700 days old, were able to be easily identified by AT8 immunostaining that can identify a phosphorylated tau protein, the core protein of neurofibrillary tangles. Nerve cells with AT8 immunostaining-positive neurofibrillary tangles, appearing in the 0.5% methyl cellulose administration control (control) group (FIG. 12 (HE stain), FIG. 13 (AT8 staining)), are neuropathologically, morphologically and immunohistochemically the same as nerve cells with AT8 immunostaining-positive neurofibrillary tangles, appearing in the mice of the compound A administration group (FIG. 14 (HE stain), FIG. 15 (AT8 staining)). Also, nerve cells with AT8 immunostaining-positive neurofibrillary tangles appearing in mice in both groups are neuropathologically, morphologically and immunohistochemically the same as nerve cells with AT8 immunostaining-positive neurofibrillary tangles appearing in the human Alzheimer's disease.

It was difficult to identify AT8 immunostaining-positive neurofibrillary tangles in the Alzheimer's disease double transgenic mouse model by the routine HE staining. With respect to the AT8 immunostaining-positive neurofibrillary tangles appearing in the human Alzheimer's disease, a part of nerve cells having AT8 immunostaining-positive neurofibrillary tangles appearing in human Alzheimer's disease has a structure that neuropathologists experienced in the human Alzheimer's disease can sometimes identify only by HE staining. Based on these empirical facts, there are non-identical points on HE staining according to these findings between AT8 immunostaining-positive neurofibrillary tangles appearing in the Alzheimer's disease double transgenic mouse model and AT8 immunostaining-positive neurofibrillary tangles appearing in human Alzheimer's disease. However, according to the fact that the detection sensitivity of neurofibrillary tangles by AT8 immunostaining is much higher than those by HE. staining in both AT8 immunostaining-positive neurofibrillary tangles appearing in the Alzheimer's disease double transgenic mouse model, and in AT8 immunostaining-positive neurofibrillary tangles appearing in human Alzheimer's disease, the evaluation therefore was conducted by AT8 immunostaining-positive neurofibrillary tangles.

2) Quantitative Analysis of the Number of the Nerve Cells with AT8 Immunostaining-Positive Neurofibrillary Tangles Neuropathological and histological characteristics of nerve cells with AT8 immunostaining-positive neurofibrillary tangles in the Alzheimer's disease double transgenic mouse model is the same as neuropathological and histological characteristics of nerve cells with AT8 immunostaining-positive neurofibrillary tangles in human Alzheimer's disease. In addition, the neuropathological and histological characteristics of nerve cells with AT8 immunostaining-positive neurofibrillary tangles in the control group and in the compound A administration group were the same. Based on these results, regarding AT8 immunostaining-positive neurofibrillary tangles, the suppressive efficacy of human Alzheimer's disease by compound A was evaluated by the quantitative analysis of nerve cells with AT8 immunostaining-positive neurofibrillary tangles.

In consideration of the common sites of nerve cells with AT8 immunostaining-positive neurofibrillary tangles in the Alzheimer's disease double transgenic mouse model, nerve cells with AT8 immunostaining-positive neurofibrillary tangles, appearing in the coronal section of cerebrum, where coronal section of cerebrum including hypothalamus and the maximum dimension of amygdaloid nucleus emerged, were measured.

The mean±standard error of the nerve cells with AT8 immunostaining-positive neurofibrillary tangles in the cerebrum 1 coronal section was 70.2±32.8 for the compound A administration group, and the nerve cells with AT8 immunostaining-positive neurofibrillary tangles in the cerebrum 1 coronal section was 287.3±29.3 for the 0.5% in the methyl cellulose administration control group.

Figure 16:
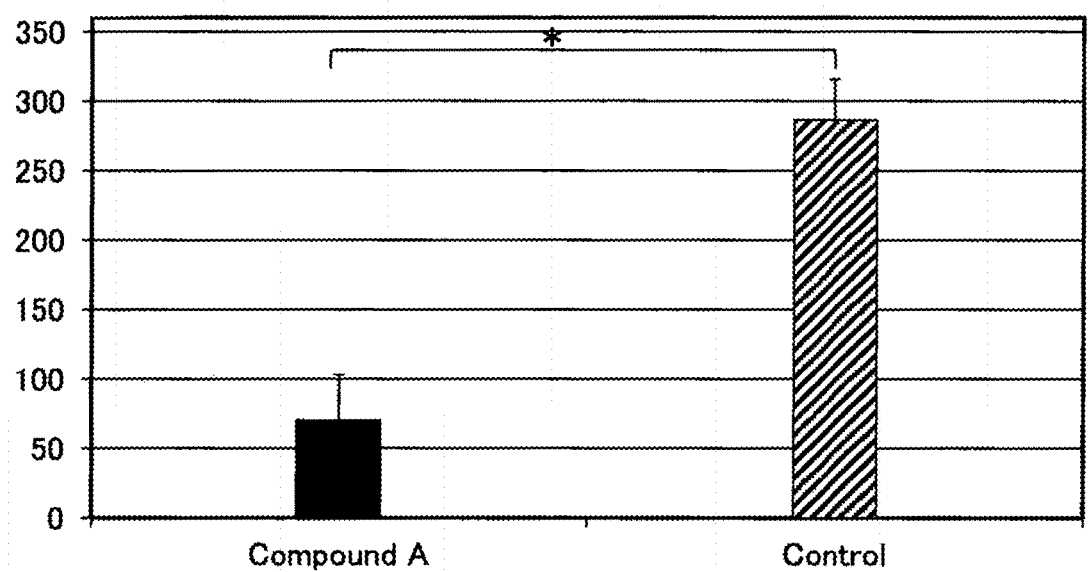
FIG. 16 shows the number of nerve cells with neurofibrillary tangle in the compound A administration group and the control group.

As a result of statistical analysis, the number of nerve cells with AT8 immunostaining-positive neurofibrillary tangles in the compound A administration group decreased significantly compared to that in the control group (p=0.014, Kruskal-Wallis test) (FIG. 16).

As explained above, it was shown from the pathological findings for the mouse model based on a causative gene of Alzheimer's disease that compound A, a selective inhibitor of the xanthine oxidase, remarkably inhibited the progress of the disease. In other words, compound A, a selective inhibitor of the xanthine oxidation-reduction enzyme, was found to inhibit significantly the number of the large senile plaques and medium senile plaques of the Alzheimer's disease mouse model, when administered orally. Also, it was found that compound A largely inhibits neurofibrillary tangles in the Alzheimer's disease mouse model, namely the accumulation of a phosphorylated tau protein by oral administration.

Similarly to compound A, the effects of the other compounds disclosed herein, for examples, compounds B-1 to B-42, C-1 to C-7, and D-1 to D-3 can be confirmed by the method described in the example.

From the above, the compound of Formula (I), (II), (III) or (IV) considered to be useful in treatment or prevention of dementia such as Alzheimer's disease.

INDUSTRIAL APPLICABILITY

The present invention can be used for treatment or prevention of dementia such as AD.

The invention claimed is:

1. A method for treating dementia comprising administering an effective amount of a 2-phenylthiazole compound represented by formula (I) or a pharmaceutically acceptable salt thereof as an active ingredient:

A 2-phenylthiazole compound represented by Formula (I):

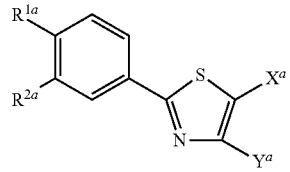

(wherein
$R^{1a}$ represents a C1-C8 alkoxy group, a morpholino group, a 4-methylpiperazin-1-yl group or a piperidino group,
$R^{2a}$ represents a nitro group or a cyano group,
$X^a$ represents a carboxyl group or a C2-C7 alkoxycarbonyl group, and
$Y^a$ represents a hydrogen atom or a C1-C6 alkyl group).

2. The method according to claim 1, wherein the compound is the following (A):
2-(3-cyano-4-isobutyloxyphenyl)-4-methyl-5-thiazolecarboxylic acid,
or a pharmaceutically acceptable salt thereof.

3. The method according to claim 1, wherein the dementia is Alzheimer's dementia.

* * * * *